(12) United States Patent
Gardner

(10) Patent No.: US 8,921,044 B2
(45) Date of Patent: **\*Dec. 30, 2014**

(54) DNA POLYMERASE VARIANTS WITH REDUCED EXONUCLEASE ACTIVITY AND USES THEREOF

(71) Applicant: New England Biolabs, Inc., Ipswich, MA (US)

(72) Inventor: Andrew Gardner, Manchester, MA (US)

(73) Assignee: New England BioLabs, Inc., Ipswich, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/247,760

(22) Filed: Apr. 8, 2014

(65) Prior Publication Data

US 2014/0296082 A1   Oct. 2, 2014

Related U.S. Application Data

(63) Continuation-in-part of application No. 13/822,724, filed as application No. PCT/US2012/037278 on May 10, 2012.

(60) Provisional application No. 61/484,731, filed on May 11, 2011.

(51) Int. Cl.
  *C12N 9/12* (2006.01)
  *C12Q 1/68* (2006.01)

(52) U.S. Cl.
  CPC .............. *C12N 9/1252* (2013.01); *C12Q 1/686* (2013.01); *C12Q 1/6869* (2013.01)
  USPC ....... 435/6.11; 435/191; 435/235.1; 435/243; 435/320.1; 435/91.2; 536/23.2

(58) Field of Classification Search
  None
  See application file for complete search history.

(56) References Cited

U.S. PATENT DOCUMENTS

| 5,489,523 | A | 2/1996 | Mathur |
| 6,008,025 | A | 12/1999 | Komatsubara et al. |
| 6,787,308 | B2 | 9/2004 | Balasubramanian et al. |
| 6,946,273 | B1 | 9/2005 | Sorge et al. |
| 7,232,656 | B2 | 6/2007 | Balasubramanian et al. |
| 7,541,170 | B2 | 6/2009 | Wang et al. |
| 7,659,100 | B2 | 2/2010 | Borns |
| 7,704,712 | B2 | 4/2010 | Borns |
| 2005/0069908 | A1 | 3/2005 | Sorge et al. |
| 2005/0123940 | A1 | 6/2005 | Sorge et al. |

FOREIGN PATENT DOCUMENTS

| EP | 0822256 | 2/1998 |
| WO | WO2007/052006 | 5/2007 |
| WO | WO2008/023179 | 2/2008 |
| WO | WO2009/131919 | 10/2009 |

OTHER PUBLICATIONS

Blanco, et al., Gene, 100:27-38 (1991).
Gardner and Jack, Nucleic Acids Research, 27(12):2545-2553 (1999).
Kong, et al., J. Biol. Chem. 268(3):1965-1975 (1993).
Southworth, et al., PNAS, USA 93:5281-5285 (1996).
Kircher, et al., Genome Biology 10(8):R83 (2009).
International Search Report for PCT/US2012/037278 dated Aug. 16, 2012.

*Primary Examiner* — Suzanne M Noakes
*Assistant Examiner* — Gerard Lacourciere
(74) *Attorney, Agent, or Firm* — New England Biolabs, Inc.; Harriet M. Strimpel

(57) ABSTRACT

Compositions and methods are described to modify Family B DNA polymerases that contain residual exonuclease activity that interferes with sequencing techniques and with detection of single nucleotide polymorphisms. The compositions are mutant proteins with reduced exonuclease activity compared with presently available "exo$^-$" polymerases, and a sensitive screening assay that enables an assessment of exonuclease activity of any synthetic DNA polymerase.

8 Claims, 13 Drawing Sheets

FIG. 11A

9° N PARENT DNA POLYMERASE exo+ (SEQ ID NO:1)

MILDTDYITENGKPVIRVFKKENGEFKIEYDRTFEPYFYALLKDDSAIEDVKKVTAKRHGTVVKVKRAEKVQKKFLGRPIEVWKLYF
NHPQDVPAIRDRIRAHPAVVDIYEYDIPFAKRYLIDKGLIPMEGDEELTMLAFDIETLYHEGEEFGTGPIMISYADGSEARVITWK
KIDLPYVDVVSTEKEMIKRPLRVVREEDPDVLITYNGDNFDFAYLKKRCEEIGIKFTLGRDGSEPKIQRMGDRFAVEVKGRIHFDLY
PVIRRTINLPTYTLEAVYEAVFGKPKEKVYAEEIAQAWESGEGLERVARYSMEDAKVTYELGREFFPMEAQISRLIGQSIMDVSRSS
TGNLVEWFLLRKAYKRNELAPNKPDERELARRRGGYAGGYVKEPERGLWDNIVYLDFRSLYPSIIITHNVSPDTLNRREGCKEYDVAP
EVGHKFCKDFPGFIPSLLGDLLEERQKIKRKMKATVDPLEKKLLDYRQRAIKLLANSFYGYYGYAKARWYCKECAESVTAWGREYIE
MVIRELEEKFGFKVLYADTDGLHATIPGADAETVKKKAKEFLKYINPKLPGLLELEYEGFYVRGFFVTKKKYAVIDEEGKITTRGLE
IVRRDWSEIAKETQARVLEAILKEGDVEEAVRLVKEVIQKEVTEKLSKYEVPPEKLVIHEQITRDLKDYKATGPHVAVAKRLAARGIKIRPG
TVISYIVLKGSGRIGDRAIPADEFDPTKHRYDAEYYIENQVLPAVERILKAFGYRKEDLRYQKTRQVGLGAWLKVGKK

FIG. 11B

VENT DNA POLYMERASE exo+ (SEQ ID NO:2)

MILDTDYITEDGKPIIRIFKKENGEFKIELDPHFQPYIYALLKDDSAITEEIKATKGERHGKIVRIVRVLDAVYKRFLGREVEVWKLIF
EHPQDVPEAMRGIKREEPAVVDIYEYDIPFTAKRYLIDKGLIPMEGDEELKLLAFDIEFYHEGDEFGKGEIIMISYADEEPARVTMK
NIDLPYVDVVSNEREMIKRFVQVVKEKDPDVLITYNGDNFDIPYLLIKRAEKKIGVTKLVLGRDKEHPEPRIQRMGDSFAVEIKGRIHFD
LFPVVRRTINLPTYTLEAVYEAVLGKTKSKLGAERIAAITMETEESMKKLAQYSMEDARATTELGKEFFPMEARLARIIGQSVMDYSR
SSTGNLVEWFLLRVAYARNELAPIKPDEEEYKRRLRTIYLGGYVREPEKGLMENIIYLDFRSLYPSIIYTHNVSPDTLREKEGCKNYD
VAPTVGCRFCKDFPGFIPSILGDLIAMRQDIKKMSTIDPIEKKMLDYRQAIKLIANSSYGYMGYPRARMYSKECAESVTAWGRH
YIEMTTREIEERKFGFKVLYADTDGFYATIPGERKPELIKKAKEPLNYINSKLPGLLELEYEGFYTTERKRYAVIDEEGRITTR
GLEVVRRDWSEIAKETQAKVLEAILKEGSVEKAVEVVRDVVEKIAKYRVPLEKLVIHEQITRDLKDYKAIGPHVAIAKRLAARGIKV
KPGTIISYIVLKGSGKISDRVLLLTEYDPRKHKYDPDYYIENQVLPAVLRIILEAFGYRKEDLRYQSSKQTGLDAWLKR

Figure 12 A-D

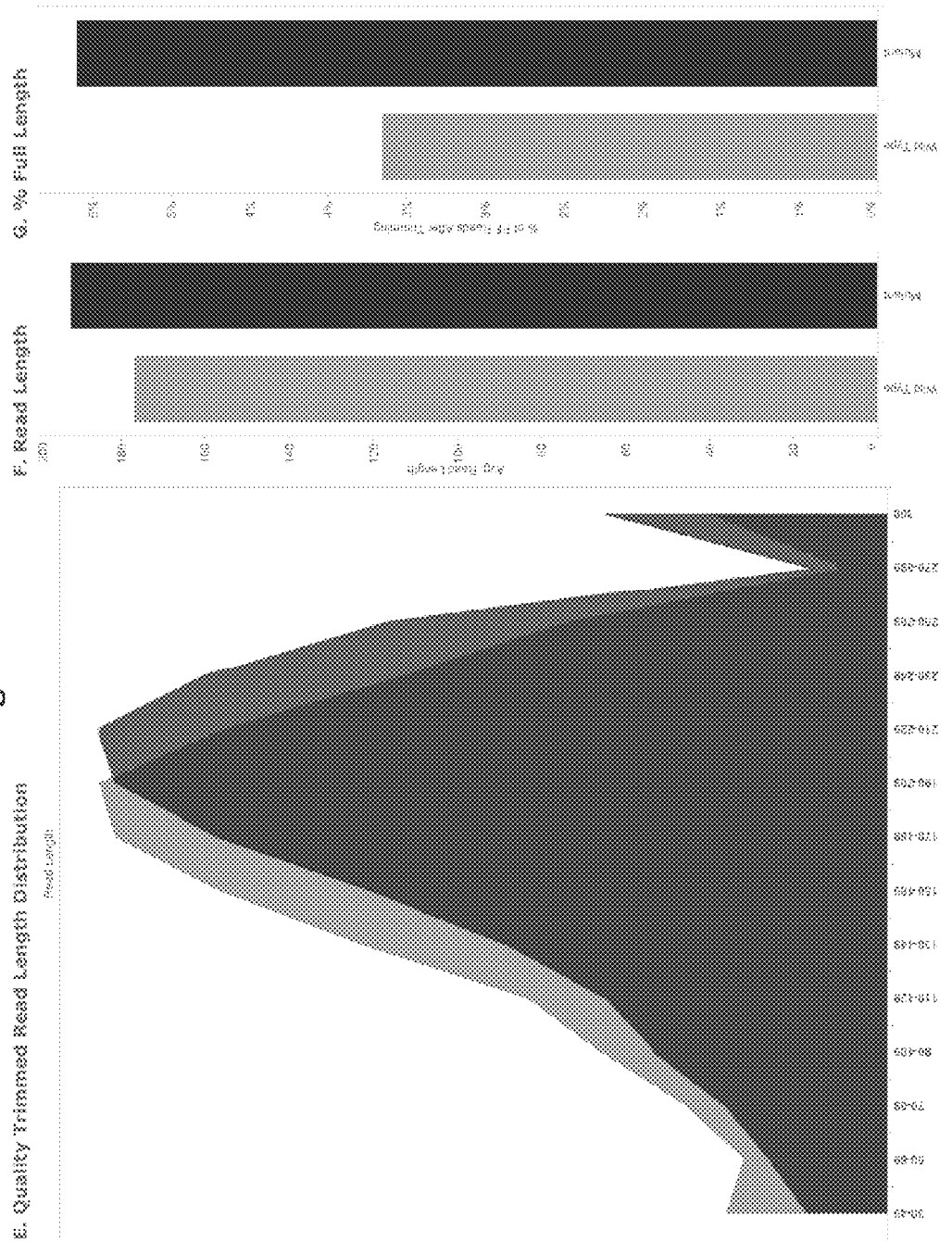

SEQUENCE LISTING

```
<160> NUMBER OF SEQ ID NOS: 12

<210> SEQ ID NO 1
<211> LENGTH: 775
<212> TYPE: PRT
<213> ORGANISM: Thermococcus sp.
<220> FEATURE:
<221> NAME/KEY: MISC_FEATURE
<222> LOCATION: (1)..(755)
<223> OTHER INFORMATION: 9 degrees N strain

<400> SEQUENCE: 1

Met Ile Leu Asp Thr Asp Tyr Ile Thr Glu Asn Gly Lys Pro Val Ile
1               5                   10                  15

Arg Val Phe Lys Lys Glu Asn Gly Glu Phe Lys Ile Glu Tyr Asp Arg
            20                  25                  30

Thr Phe Glu Pro Tyr Phe Tyr Ala Leu Leu Lys Asp Asp Ser Ala Ile
        35                  40                  45

Glu Asp Val Lys Lys Val Thr Ala Lys Arg His Gly Thr Val Val Lys
    50                  55                  60

Val Lys Arg Ala Glu Lys Val Gln Lys Lys Phe Leu Gly Arg Pro Ile
65                  70                  75                  80

Glu Val Trp Lys Leu Tyr Phe Asn His Pro Gln Asp Val Pro Ala Ile
                85                  90                  95

Arg Asp Arg Ile Arg Ala His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Thr Met Leu Ala Phe Asp Ile Glu Thr
    130                 135                 140

Leu Tyr His Glu Gly Glu Glu Phe Gly Thr Gly Pro Ile Leu Met Ile
145                 150                 155                 160

Ser Tyr Ala Asp Gly Ser Glu Ala Arg Val Ile Thr Trp Lys Lys Ile
                165                 170                 175

Asp Leu Pro Tyr Val Asp Val Val Ser Thr Glu Lys Glu Met Ile Lys
            180                 185                 190

Arg Phe Leu Arg Val Val Arg Glu Lys Asp Pro Asp Val Leu Ile Thr
        195                 200                 205

Tyr Asn Gly Asp Asn Phe Asp Phe Ala Tyr Leu Lys Lys Arg Cys Glu
    210                 215                 220

Glu Leu Gly Ile Lys Phe Thr Leu Gly Arg Asp Gly Ser Glu Pro Lys
225                 230                 235                 240

Ile Gln Arg Met Gly Asp Arg Phe Ala Val Glu Val Lys Gly Arg Ile
```

```
                    245                 250                 255
His Phe Asp Leu Tyr Pro Val Ile Arg Arg Thr Ile Asn Leu Pro Thr
                260                 265                 270
Tyr Thr Leu Glu Ala Val Tyr Glu Ala Val Phe Gly Lys Pro Lys Glu
            275                 280                 285
Lys Val Tyr Ala Glu Glu Ile Ala Gln Ala Trp Glu Ser Gly Glu Gly
        290                 295                 300
Leu Glu Arg Val Ala Arg Tyr Ser Met Glu Asp Ala Lys Val Thr Tyr
305                 310                 315                 320
Glu Leu Gly Arg Glu Phe Phe Pro Met Glu Ala Gln Leu Ser Arg Leu
                325                 330                 335
Ile Gly Gln Ser Leu Trp Asp Val Ser Arg Ser Ser Thr Gly Asn Leu
                340                 345                 350
Val Glu Trp Phe Leu Leu Arg Lys Ala Tyr Lys Arg Asn Glu Leu Ala
            355                 360                 365
Pro Asn Lys Pro Asp Glu Arg Glu Leu Ala Arg Arg Gly Gly Tyr
        370                 375                 380
Ala Gly Gly Tyr Val Lys Glu Pro Glu Arg Gly Leu Trp Asp Asn Ile
385                 390                 395                 400
Val Tyr Leu Asp Phe Arg Ser Leu Tyr Pro Ser Ile Ile Ile Thr His
                405                 410                 415
Asn Val Ser Pro Asp Thr Leu Asn Arg Glu Gly Cys Lys Glu Tyr Asp
                420                 425                 430
Val Ala Pro Glu Val Gly His Lys Phe Cys Lys Asp Phe Pro Gly Phe
            435                 440                 445
Ile Pro Ser Leu Leu Gly Asp Leu Leu Glu Glu Arg Gln Lys Ile Lys
        450                 455                 460
Arg Lys Met Lys Ala Thr Val Asp Pro Leu Glu Lys Lys Leu Leu Asp
465                 470                 475                 480
Tyr Arg Gln Arg Ala Ile Lys Ile Leu Ala Asn Ser Phe Tyr Gly Tyr
                485                 490                 495
Tyr Gly Tyr Ala Lys Ala Arg Trp Tyr Cys Lys Glu Cys Ala Glu Ser
                500                 505                 510
Val Thr Ala Trp Gly Arg Glu Tyr Ile Glu Met Val Ile Arg Glu Leu
            515                 520                 525
Glu Glu Lys Phe Gly Phe Lys Val Leu Tyr Ala Asp Thr Asp Gly Leu
        530                 535                 540
His Ala Thr Ile Pro Gly Ala Asp Ala Glu Thr Val Lys Lys Lys Ala
545                 550                 555                 560
Lys Glu Phe Leu Lys Tyr Ile Asn Pro Lys Leu Pro Gly Leu Leu Glu
                565                 570                 575
Leu Glu Tyr Glu Gly Phe Tyr Val Arg Gly Phe Phe Val Thr Lys Lys
                580                 585                 590
Lys Tyr Ala Val Ile Asp Glu Glu Gly Lys Ile Thr Thr Arg Gly Leu
            595                 600                 605
Glu Ile Val Arg Arg Asp Trp Ser Glu Ile Ala Lys Glu Thr Gln Ala
        610                 615                 620
Arg Val Leu Glu Ala Ile Leu Lys His Gly Asp Val Glu Glu Ala Val
625                 630                 635                 640
Arg Ile Val Lys Glu Val Thr Glu Lys Leu Ser Lys Tyr Glu Val Pro
                645                 650                 655
Pro Glu Lys Leu Val Ile His Glu Gln Ile Thr Arg Asp Leu Arg Asp
                660                 665                 670
```

```
Tyr Lys Ala Thr Gly Pro His Val Ala Val Lys Arg Leu Ala Ala
            675                 680                 685

Arg Gly Val Lys Ile Arg Pro Gly Thr Val Ile Ser Tyr Ile Val Leu
    690                 695                 700

Lys Gly Ser Gly Arg Ile Gly Asp Arg Ala Ile Pro Ala Asp Glu Phe
705                 710                 715                 720

Asp Pro Thr Lys His Arg Tyr Asp Ala Glu Tyr Tyr Ile Glu Asn Gln
                725                 730                 735

Val Leu Pro Ala Val Glu Arg Ile Leu Lys Ala Phe Gly Tyr Arg Lys
                740                 745                 750

Glu Asp Leu Arg Tyr Gln Lys Thr Lys Gln Val Gly Leu Gly Ala Trp
                755                 760                 765

Leu Lys Val Lys Gly Lys Lys
            770             775

<210> SEQ ID NO 2
<211> LENGTH: 774
<212> TYPE: PRT
<213> ORGANISM: Thermococcus litoralis

<400> SEQUENCE: 2

Met Ile Leu Asp Thr Asp Tyr Ile Thr Lys Asp Gly Lys Pro Ile Ile
1               5                   10                  15

Arg Ile Phe Lys Lys Glu Asn Gly Glu Phe Lys Ile Glu Leu Asp Pro
                20                  25                  30

His Phe Gln Pro Tyr Ile Tyr Ala Leu Leu Lys Asp Asp Ser Ala Ile
            35                  40                  45

Glu Glu Ile Lys Ala Ile Lys Gly Glu Arg His Gly Lys Thr Val Arg
    50                  55                  60

Val Leu Asp Ala Val Lys Val Arg Lys Lys Phe Leu Gly Arg Glu Val
65                  70                  75                  80

Glu Val Trp Lys Leu Ile Phe Glu His Pro Gln Asp Val Pro Ala Met
                85                  90                  95

Arg Gly Lys Ile Arg Glu His Pro Ala Val Val Asp Ile Tyr Glu Tyr
            100                 105                 110

Asp Ile Pro Phe Ala Lys Arg Tyr Leu Ile Asp Lys Gly Leu Ile Pro
        115                 120                 125

Met Glu Gly Asp Glu Glu Leu Lys Leu Leu Ala Phe Asp Ile Glu Thr
    130                 135                 140

Phe Tyr His Glu Gly Asp Glu Phe Gly Lys Gly Glu Ile Ile Met Ile
145                 150                 155                 160

Ser Tyr Ala Asp Glu Glu Glu Ala Arg Val Ile Thr Trp Lys Asn Ile
                165                 170                 175

Asp Leu Pro Tyr Val Asp Val Val Ser Asn Glu Arg Glu Met Ile Lys
            180                 185                 190

Arg Phe Val Gln Val Val Lys Glu Lys Asp Pro Asp Val Ile Ile Thr
        195                 200                 205

Tyr Asn Gly Asp Asn Phe Asp Leu Pro Tyr Leu Ile Lys Arg Ala Glu
    210                 215                 220

Lys Leu Gly Val Arg Leu Val Leu Gly Arg Asp Lys Glu His Pro Glu
225                 230                 235                 240

Pro Lys Ile Gln Arg Met Gly Asp Ser Phe Ala Val Glu Ile Lys Gly
                245                 250                 255

Arg Ile His Phe Asp Leu Phe Pro Val Val Arg Arg Thr Ile Asn Leu
```

```
                260             265             270
Pro Thr Tyr Thr Leu Glu Ala Val Tyr Glu Ala Val Leu Gly Lys Thr
            275             280             285
Lys Ser Lys Leu Gly Ala Glu Glu Ile Ala Ala Ile Trp Glu Thr Glu
        290             295             300
Glu Ser Met Lys Lys Leu Ala Gln Tyr Ser Met Glu Asp Ala Arg Ala
305             310             315             320
Thr Tyr Glu Leu Gly Lys Glu Phe Phe Pro Met Glu Ala Glu Leu Ala
                325             330             335
Lys Leu Ile Gly Gln Ser Val Trp Asp Val Ser Arg Ser Ser Thr Gly
            340             345             350
Asn Leu Val Glu Trp Tyr Leu Leu Arg Val Ala Tyr Ala Arg Asn Glu
        355             360             365
Leu Ala Pro Asn Lys Pro Asp Glu Glu Tyr Lys Arg Arg Leu Arg
    370             375             380
Thr Thr Tyr Leu Gly Gly Tyr Val Lys Glu Pro Glu Lys Gly Leu Trp
385             390             395             400
Glu Asn Ile Ile Tyr Leu Asp Phe Arg Ser Leu Tyr Pro Ser Ile Ile
                405             410             415
Val Thr His Asn Val Ser Pro Asp Thr Leu Glu Lys Glu Gly Cys Lys
            420             425             430
Asn Tyr Asp Val Ala Pro Ile Val Gly Tyr Arg Phe Cys Lys Asp Phe
        435             440             445
Pro Gly Phe Ile Pro Ser Ile Leu Gly Asp Leu Ile Ala Met Arg Gln
    450             455             460
Asp Ile Lys Lys Lys Met Lys Ser Thr Ile Asp Pro Ile Glu Lys Lys
465             470             475             480
Met Leu Asp Tyr Arg Gln Arg Ala Ile Lys Leu Leu Ala Asn Ser Tyr
                485             490             495
Tyr Gly Tyr Met Gly Tyr Pro Lys Ala Arg Trp Tyr Ser Lys Glu Cys
            500             505             510
Ala Glu Ser Val Thr Ala Trp Gly Arg His Tyr Ile Glu Met Thr Ile
        515             520             525
Arg Glu Ile Glu Glu Lys Phe Gly Phe Lys Val Leu Tyr Ala Asp Thr
    530             535             540
Asp Gly Phe Tyr Ala Thr Ile Pro Gly Glu Lys Pro Glu Leu Ile Lys
545             550             555             560
Lys Lys Ala Lys Glu Phe Leu Asn Tyr Ile Asn Ser Lys Leu Pro Gly
                565             570             575
Leu Leu Glu Leu Glu Tyr Glu Gly Phe Tyr Leu Arg Gly Phe Phe Val
            580             585             590
Thr Lys Lys Arg Tyr Ala Val Ile Asp Glu Glu Gly Arg Ile Thr Thr
        595             600             605
Arg Gly Leu Glu Val Val Arg Arg Asp Trp Ser Glu Ile Ala Lys Glu
    610             615             620
Thr Gln Ala Lys Val Leu Glu Ala Ile Leu Lys Glu Gly Ser Val Glu
625             630             635             640
Lys Ala Val Glu Val Val Arg Asp Val Val Lys Ile Ala Lys Tyr
                645             650             655
Arg Val Pro Leu Glu Lys Leu Val Ile His Glu Gln Ile Thr Arg Asp
            660             665             670
Leu Lys Asp Tyr Lys Ala Ile Gly Pro His Val Ala Ile Ala Lys Arg
        675             680             685
```

```
Leu Ala Ala Arg Gly Ile Lys Val Lys Pro Gly Thr Ile Ile Ser Tyr
        690                 695                 700

Ile Val Leu Lys Gly Ser Gly Lys Ile Ser Asp Arg Val Ile Leu Leu
705                 710                 715                 720

Thr Glu Tyr Asp Pro Arg Lys His Lys Tyr Asp Pro Asp Tyr Tyr Ile
                725                 730                 735

Glu Asn Gln Val Leu Pro Ala Val Leu Arg Ile Leu Glu Ala Phe Gly
            740                 745                 750

Tyr Arg Lys Glu Asp Leu Arg Tyr Gln Ser Ser Lys Gln Thr Gly Leu
        755                 760                 765

Asp Ala Trp Leu Lys Arg
        770

<210> SEQ ID NO 3
<211> LENGTH: 7
<212> TYPE: PRT
<213> ORGANISM: Thermococcus sp.
<220> FEATURE:
<221> NAME/KEY: MISC_FEATURE
<222> LOCATION: (1)..(7)
<223> OTHER INFORMATION: Exo Motif I corresponding to residues 138-144
      in SEQ ID NO:1

<400> SEQUENCE: 3

Leu Ala Phe Asp Ile Glu Thr
1               5

<210> SEQ ID NO 4
<211> LENGTH: 9
<212> TYPE: PRT
<213> ORGANISM: Thermococcus sp.
<220> FEATURE:
<221> NAME/KEY: MISC_FEATURE
<222> LOCATION: (1)..(9)
<223> OTHER INFORMATION: Exo Motif II corresponding to residues 207-215
      in SEQ ID NO:1

<400> SEQUENCE: 4

Ile Thr Tyr Asn Gly Asp Asn Phe Asp
1               5

<210> SEQ ID NO 5
<211> LENGTH: 6
<212> TYPE: PRT
<213> ORGANISM: Thermococcus sp.
<220> FEATURE:
<221> NAME/KEY: MISC_FEATURE
<222> LOCATION: (1)..(6)
<223> OTHER INFORMATION: Exo Motif III corresponding to residues 311-316
      in SEQ ID NO:1

<400> SEQUENCE: 5

Tyr Ser Met Glu Asp Ala
1               5

<210> SEQ ID NO 6
<211> LENGTH: 11
<212> TYPE: PRT
<213> ORGANISM: Thermococcus sp.
<220> FEATURE:
<221> NAME/KEY: MISC_FEATURE
<222> LOCATION: (1)..(11)
<223> OTHER INFORMATION: Exo Motif IV corresponding to residues 269-279
      in SEQ ID NO:1
<220> FEATURE:
<221> NAME/KEY: MISC_FEATURE
```

```
<222> LOCATION: (9)..(9)
<223> OTHER INFORMATION: Xaa can be any naturally occurring amino acid

<400> SEQUENCE: 6

Asn Leu Pro Thr Tyr Thr Leu Glu Xaa Val Tyr
1               5                   10

<210> SEQ ID NO 7
<211> LENGTH: 6
<212> TYPE: PRT
<213> ORGANISM: Thermococcus sp.
<220> FEATURE:
<221> NAME/KEY: MISC_FEATURE
<222> LOCATION: (1)..(7)
<223> OTHER INFORMATION: Exo Motif V corresponding to residues 241-246
      in SEQ ID NO:1

<400> SEQUENCE: 7

Ile Gln Arg Met Gly Asp
1               5

<210> SEQ ID NO 8
<211> LENGTH: 7
<212> TYPE: PRT
<213> ORGANISM: Thermococcus sp.
<220> FEATURE:
<221> NAME/KEY: MISC_FEATURE
<222> LOCATION: (1)..(7)
<223> OTHER INFORMATION: Exo Motif VI corresponding to residues 286-292
      in SEQ ID NO:1

<400> SEQUENCE: 8

Pro Lys Glu Lys Val Tyr Ala
1               5

<210> SEQ ID NO 9
<211> LENGTH: 24
<212> TYPE: DNA
<213> ORGANISM: artificial
<220> FEATURE:
<223> OTHER INFORMATION: primer

<400> SEQUENCE: 9
cgccagggtt ttcccagtca cgac                                          24

<210> SEQ ID NO 10
<211> LENGTH: 44
<212> TYPE: DNA
<213> ORGANISM: artificial
<220> FEATURE:
<223> OTHER INFORMATION: template

<400> SEQUENCE: 10
aaccggttac gtacgtacgt gtcgtgactg ggaaaaccct ggcg                     44

<210> SEQ ID NO 11
<211> LENGTH: 12
<212> TYPE: PRT
<213> ORGANISM: unknown
<220> FEATURE:
<223> OTHER INFORMATION: motif, which can exist in many organisms
<220> FEATURE:
<221> NAME/KEY: MISC_FEATURE
<222> LOCATION: (1)..(1)
<223> OTHER INFORMATION: Xaa can be any non-polar amino acid (e.g.,
      glycine, alanine, valine, leucine, isoleucine, proline,
      methionine, phenylalanine, tryptophan)
<220> FEATURE:
<221> NAME/KEY: misc_feature
```

```
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be any polar amino acid (e.g., serine,
      threonine, asparagine, glutamine, cysteine, tyrosine, aspartic
      acid, glutamic acid, lysine, arginine, histidine)
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (10)..(11)
<223> OTHER INFORMATION: Xaa can be any non-polar amino acid (e.g.,
      glycine, alanine, valine, leucine, isoleucine, proline,
      methionine, phenylalanine, tryptophan)

<400> SEQUENCE: 11

Xaa Xaa Tyr Asn Xaa Xaa Xaa Phe Asp Xaa Xaa Tyr
1               5                   10

<210> SEQ ID NO 12
<211> LENGTH: 6
<212> TYPE: PRT
<213> ORGANISM: Thermococcus litoralis
<220> FEATURE:
<221> NAME/KEY: MISC_FEATURE
<222> LOCATION: (1)..(6)
<223> OTHER INFORMATION: corresponds to amino acid residues 287-292 in
      SEQ ID NO:2

<400> SEQUENCE: 12

Thr Lys Ser Lys Leu Gly
1               5
```

DNA POLYMERASE VARIANTS WITH REDUCED EXONUCLEASE ACTIVITY AND USES THEREOF

CROSS-REFERENCE

This application is a continuation-in-part of U.S. application Ser. No. 13/822,724 filed Mar. 13, 2013 that is incorporated in entirety by reference. U.S. application Ser. No. 13/822,724 is a §371 application of international application number PCT/US2012/037278 filed on May 10, 2012, which claims priority from U.S. provisional application No. 61/484,731 filed May 11, 2011, herein incorporated by reference.

BACKGROUND

DNA polymerases catalyze DNA polymerization. In addition, a subset of Family A, B, and D DNA polymerases also have proofreading 3' to 5' (3'-5') exonuclease activity and are referred to as exo+ polymerases (Blanco et al. *Gene* 100:27-38 (1991)). When a DNA polymerase incorporates an incorrect or modified nucleotide, for example, in a primer strand, it detects structural perturbations caused by mispairing or nucleotide modification and transfers the primer strand from the polymerase domain to the 3'-5' exonuclease active site.

These polymerases have been extensively employed in molecular biology applications such as single-molecule sequencing, sequencing by synthesis, and single nucleotide polymorphism (SNP) detection. Modified nucleotides that may be incorporated by DNA polymerases in these methods include nucleotide terminators (dideoxynucleotide triphosphates (ddNTPs), and acyclic-nucleoside triphosphates (acycloNTPs)), reversible nucleotide terminators (3'-O-azidomethyl-ddNTPs, 3'-O-amino-ddNTPs, and Lightning Terminators™ (Lasergen, Inc., Houston, Tex.)) and tagged nucleotides (biotin-deoxyuridine triphosphates (biotin-dUTPs)). Once incorporated, these modified nucleotides can be hydrolyzed by DNA polymerases having exonuclease activity, compromising the incorporation regimen.

Presumptive exonuclease minus (exo−) DNA polymerase mutants have been described in the literature and are commercially available. The commercial exo− archaeal DNA polymerase mutants have a single mutation in Motif I and/or II, or a double mutation in Motif I, namely D141A and E143A, that reportedly abolishes detectible exonuclease activity (see for example, VENT® (*Thermococcus litoralis*) (Kong et al. *J. Biol. Chem.* 268(3):1965-1975) (New England Biolabs, Inc. (NEB), Ipswich, Mass.); *Thermococcus* JDF-3 (U.S. Pat. No. 6,946,273, U.S. 2005-0069908); KODI (*Thermococcus kodakaraensis*) (U.S. Pat. No. 6,008,025); Pfu (*Pyrococcus furiosus*,) (U.S. Pat. No. 5,489,523, U.S. Pat. No. 7,704,712, and U.S. Pat. No. 7,659,100); and 9° N. (*Thermococcus* sp.) (U.S. 2005-0123940 and Southworth et al. *Proc Natl Acad Sci USA* 93:5281-5285 (1996)).

SUMMARY

In general in a first aspect, a variant of a parent polymerase is described wherein the parent polymerase has at least 90% sequence homology with SEQ ID NO:1 and/or SEQ ID NO:2 and wherein a difference between the parent polymerase and the variant comprises at least one amino acid mutation in SEQ ID NO:5 and at least one amino acid mutation in at least one amino acid sequence selected from SEQ ID NOS: 3, 4, 6, 7 and 8.

Various embodiments include one or more of the following features:

The difference between variant and parent polymerases comprises at least one amino acid mutation in SEQ ID NO:5 and at least one amino acid mutation in at least one amino acid sequence selected from SEQ ID NOS:3, 4, and 6-8.

The difference between variant and parent polymerases further comprises at least two amino acid mutations in SEQ ID NO:3.

The difference between variant and parent polymerases further comprises a ratio of exonuclease activity/polymerase activity of less than $1.5 \times 10^{-6}$.

The difference between variant and parent polymerases further comprises an exonuclease activity of less than 0.01 units/mg.

The parent polymerase has an amino acid sequence with at least 90% sequence homology with SEQ ID NOS:3-7.

The variant polymerase has an amino acid sequence with at least 80% sequence identity to SEQ ID NOS:3-7.

The variant polymerase has at least one mutation in SEQ ID NO:5 corresponding to position 315 in SEQ ID NO:1 where the amino acid at that position is not Asp(D).

The variant has an amino acid mutation in SEQ ID NO:5 and a plurality of amino acid mutations in SEQ ID NO:3.

In one aspect, a variant is provided which may be characterized by one or more properties selected from: reducing average phasing by 1%-51%, for example, 1%-40%, for example 1%-30%, for example, 1%-20%, for example, 1%-15%, for example 1%-10%, for example, 1%-8% compared to the parent polymerase; increasing average sequencing read quality by 7%-75% for example, 7%-65%, for example, 7%-55%, for example, 7%-45%, for example, 7%-35%, for example, 7%-25% compared to parent enzyme; increasing average sequencing read length by 1%-200% for example, 1%-150%, 1%-100%, 1%-80%, 15-70%. 1%-60%, 1%-50%, or 1%-40% and increasing average full length sequencing reads by 25%-200%, 25%-150%, 25%-100%, or 25%-80%.

For example, the variant may be have one or more properties selected from: reducing average phasing by at least 1%-10% compared to the parent polymerase; increasing average sequencing read quality by at least 10%-50% compared to parent enzyme; increasing average sequencing read length by at least 5%-20% and increasing average full length sequencing reads by at least 25%-100%.

In general in a second aspect, a DNA is described that encodes a protein having at least 90% sequence identity with SEQ ID NO:1 or 2, the DNA having a plurality of mutations causing a change in at least one amino acid in SEQ ID NO:5 and a change in at least one amino acid in an amino acid sequence selected from SEQ ID NOS:3, 4, 6 and 8.

Various embodiments include one or more of the following features:

A DNA with a mutation causing a change in the amino acid at position 315, and optionally at one or more positions selected from 141, 143 and 215, for example D315, D141, D143, and D215 in the parent polymerase;

A plasmid, comprising: the DNA described above;

A prokaryotic cell transformed with the plasmid described above; and

A bacteriophage containing the DNA described above.

In general in a third aspect, a method of amplifying DNA in the absence of exonuclease activity is described that includes combining a variant described above with a template DNA and a primer; and amplifying the DNA.

In general in a fourth aspect, a method is provided of sequencing a polynucleotide that includes combining a variant polymerase described above with a template polynucleotide and at least one primer to form a hybridized polynucleotide; permitting the variant polymerase to incorporate into the template-primer hybrid, a modified nucleotide that is complementary to a nucleoside at the corresponding position on the template; and identifying the nucleoside at the corresponding position on the template.

In one aspect, the variant polymerase is characterized by of one or more properties selected from: reducing average phasing by 1%-51%, for example, 1%-40%, for example 1%-30%, for example, 1%-20%, for example, 1%-15%, for example 1%-10%, for example, 1%-8% compared to the parent polymerase; increasing average sequencing read quality by 7%-75% for example, 7%-65%, for example, 7%-55%, for example, 7%-45%, for example, 7%-35%, for example, 7%-25% compared to parent enzyme; increasing average sequencing read length by 1%-200% for example, 1%-150%, 1%-100%, 1%-80%, 15-70%. 1%-60%, 1%-50%, or 1%-40% and increasing average full length sequencing reads by 25%-200%, 25%-150%, 25%-100%, or 25%-80%.

In another aspect, the variant is characterized by one or more properties selected from: reducing average phasing by at least 1%-10% compared to the parent polymerase; increasing average sequencing read quality by at least 10%-50% compared to parent enzyme; increasing average sequencing read length by at least 5%-20% and increasing average full length sequencing reads by at least 25%-100%.

In one aspect, the method described by the fourth aspect may include one or more of the following steps: reducing average phasing by 1%-51%, for example, 1%-40%, for example 1%-30%, for example, 1%-20%, for example, 1%-15%, for example 1%-10%, for example, 1%-8% compared to the parent polymerase; increasing average sequencing read quality by 7%-75% for example, 7%-65%, for example, 7%-55%, for example, 7%-45%, for example, 7%-35%, for example, 7%-25% compared to parent enzyme; increasing average sequencing read length by 1%-200% for example, 1%-150%, 1%-100%, 1%-80%, 15-70%. 1%-60%, 1%-50%, or 1%-40% and increasing average full length sequencing reads by 25%-200%, 25%-150%, 25%-100%, or 25%-80%.

In another aspect, the method of the fourth aspect may include one or more of the following steps: reducing average phasing by at least 1%-10% compared to the parent polymerase; increasing average sequencing read quality by at least 10%-50% compared to parent enzyme; increasing average sequencing read length by at least 5%-20% and increasing average full length sequencing reads by at least 25%-100%.

BRIEF DESCRIPTION OF THE DRAWINGS

FIG. 4A: Four variants of a purified 9° N DNA polymerase from archaeon *Thermococcus* sp. 9° N-7 [TaxId: 35749] were analyzed by SDS-polyacrylamide gels (PAGE). A single band was observed at the expected molecular weight for each sample, showing that any observed exonuclease activity derives from the polymerase and not from contaminant enzymes.

FIG. 5A is a schematic illustrating two pathways for removal of a deoxyadenosine-5'-monophosphate (dAMP) residue from the 3' end of a primer, either exonuclease action (yielding dAMP or p(dA)) or pyrophosphorylsis in the presence of inorganic pyrophosphate (PPi), yielding deoxyadenosine triphosphate (dATP or ppp(dA)).

FIG. 5B is a schematic showing that when the 3' dAMP has an [alpha-$^{32}$P] label, the digestion products can be visualized and quantified after separation by polyethyleneimine (PEI)-cellulose (Merck, Whitehouse Station, N.J.) thin layer chromatography (TLC).

FIG. 5C shows different amounts of pyrophosphorlysis when exo$^+$ and exo$^-$ forms of DNA polymerase VENT are compared.

Lane 1 shows separation of dATP and dAMP.

Lanes 2 and 3 are duplicate samples of undigested 3'-labeled primer.

Lanes 4 and 5 show the products resulting from incubation with unmodified VENT (exo$^+$) DNA polymerase, which possesses exonuclease activity. dAMP is the sole product detected.

Lanes 6 and 7 show dATP is released upon incubation with the modified VENT (exo$^-$) DNA polymerase (D141A/E143A) in the presence of an excess of PPi.

Figure 5:
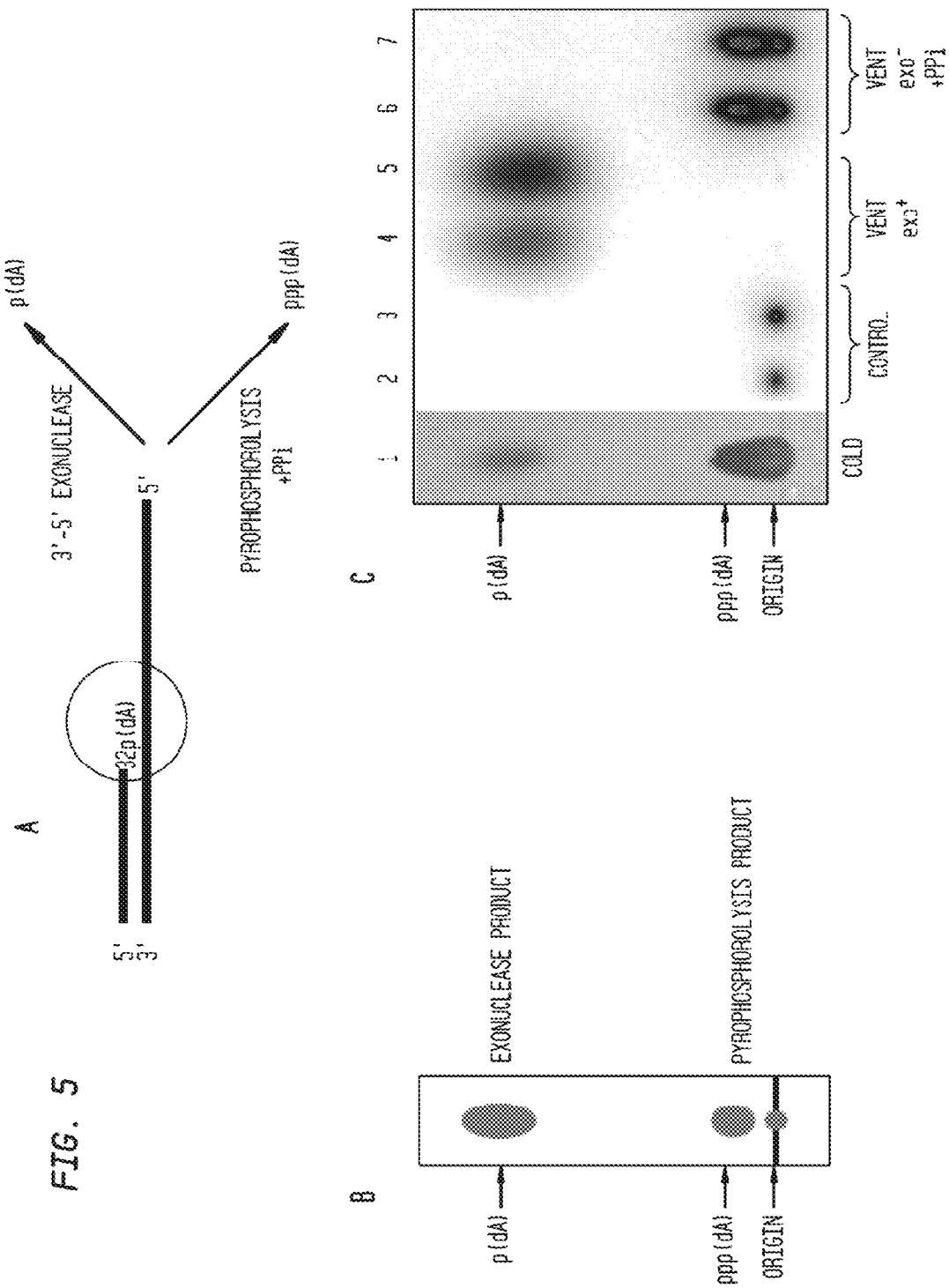
FIGS. 5A-C show that exonuclease activity and pyrophosphorylsis can be distinguished.
Figure 6:
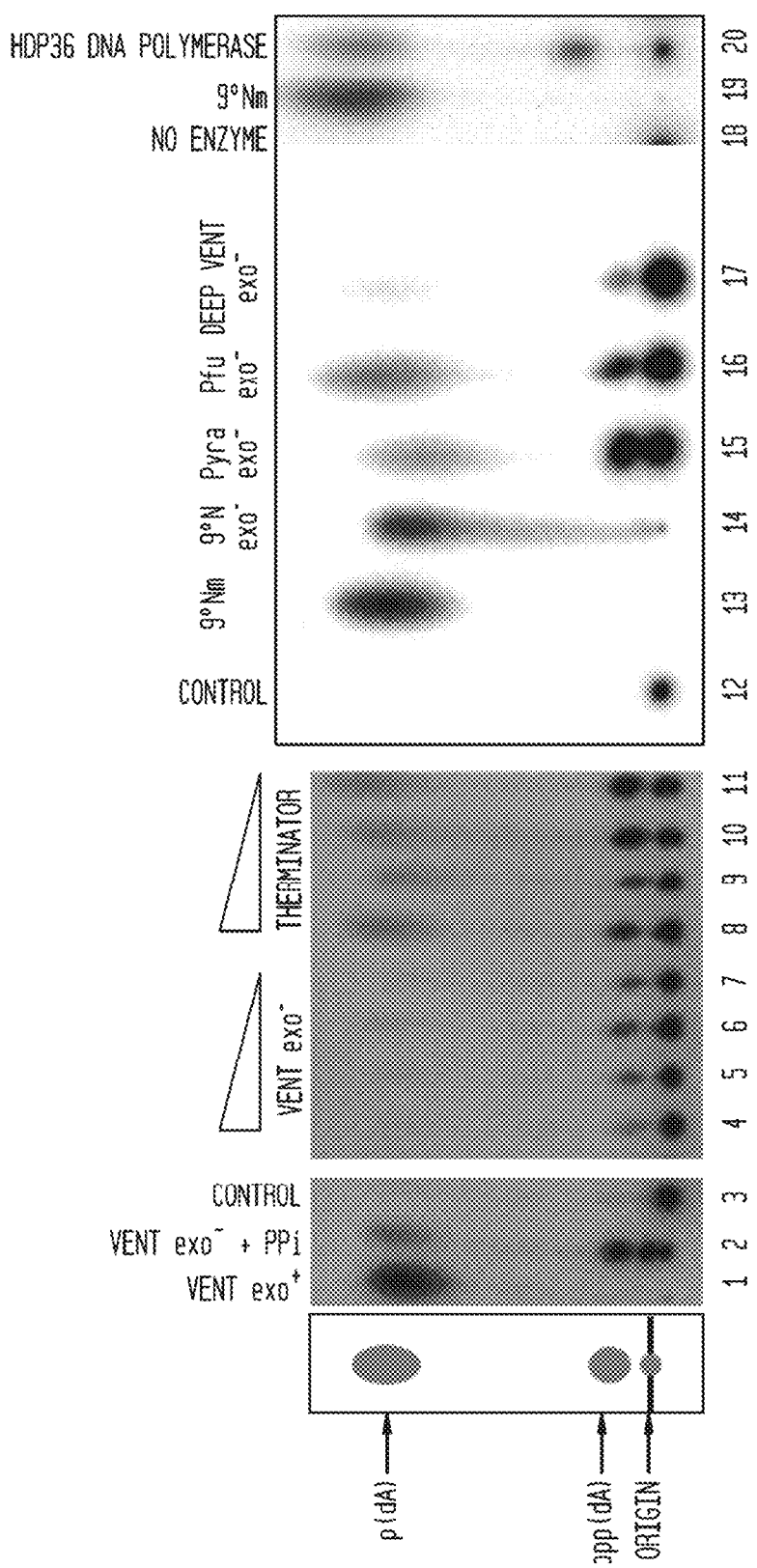

FIG. 6 shows that commercially available archaeal (exo$^-$) DNA polymerase preparations exhibit exonuclease activity using the assay of FIG. 5A. The results of TLC separation of reaction products, as described in FIGS. 5B-C, are provided using various polymerases.

Lane 1 demonstrates complete exonuclease hydrolysis of the substrate by the unmodified VENT (exo$^+$) DNA polymerase.

Lane 2 demonstrates mixed exonuclease and pyrophosphorylsis products produced by VENT (exo$^-$) DNA polymerase in the presence of PPi.

Lane 3 is a control and displays the starting material incubated without added polymerase.

Lanes 4-7 show exonuclease activity associated with decreasing concentrations of VENT (exo$^-$) DNA polymerase.

Lanes 8-11 show exonulcease activity associated with decreasing concentrations of Therminator™ DNA polymerase ((Exo Motif I: D141A/E143A) and A485L), (NEB, Ipswich, Mass.). In both cases, significant amounts of dAMP and dATP are observed.

Lane 12 is a control and displays the starting material incubated without added polymerase.

Lanes 13-20 show exonuclease activity in commercial (exo$^-$) DNA polymerases which have 1 or 2 mutations in Motif I Lane 13: 9° Nm. (E143D) which is known to have about 5% of the exonuclease nuclease activity of 9° N (exo⁺) DNA polymerase.

Lane 14: 9° N (exo⁻) DNA polymerase (D141A/E143A);
Lane 15: Pyra (exo⁻) DNA polymerase (D141A/E143A);
Lane 16: Pfu (exo⁻) DNA polymerase (D141A/E143A);
Lane 17: DEEP VENT™ (exo⁻) DNA polymerase (D141A/E143A) (NEB, Ipswich, Mass.); Lane 18: a control and displays the starting material incubated without added polymerase;
Lane 19: 9° N$_m$. DNA polymerase (E143D); and
Lane 20: Illumina® HDP36 DNA polymerase (D141A/E143A) (Illumina, San Diego, Calif.).

Figure 7:
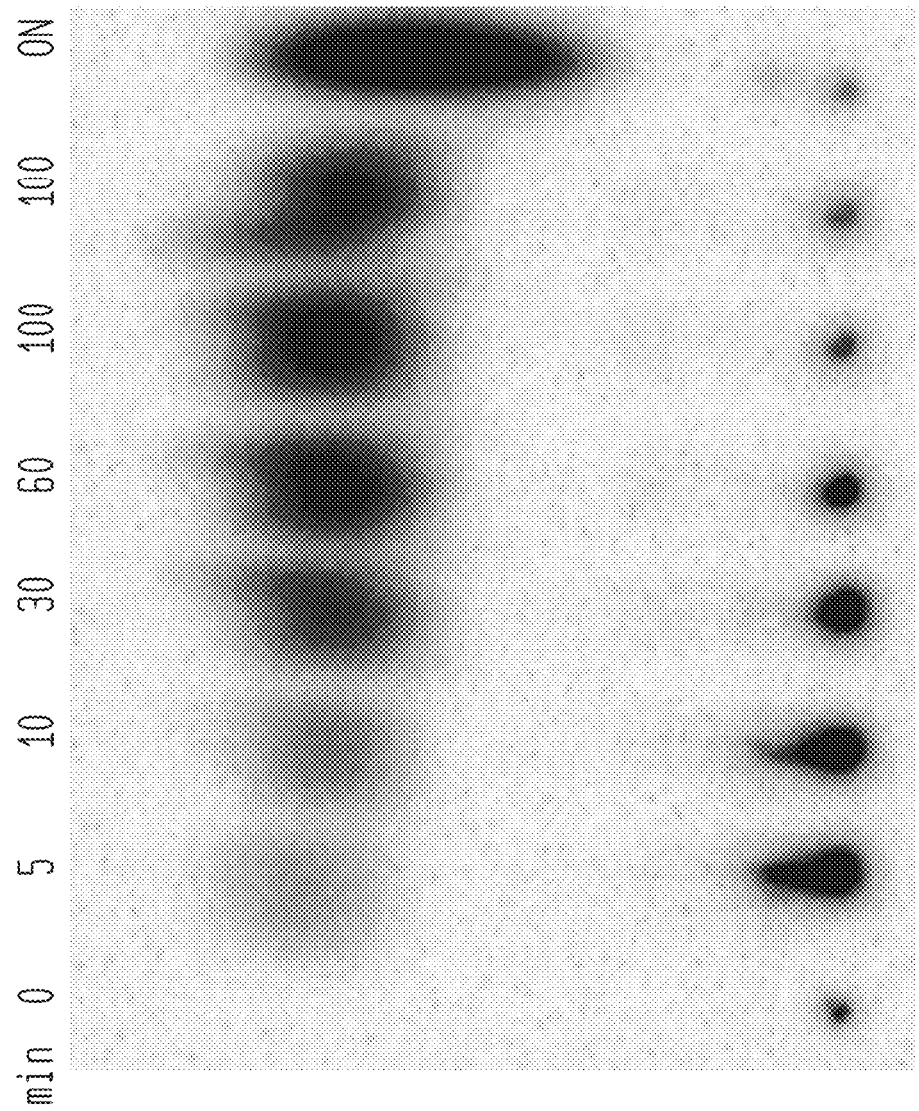

FIG. 7 shows residual exonuclease activity in 9° N (exo⁻) DNA polymerase (D141/E143A) over time. Samples were analyzed at 0, 5, 10, 30, 60, 100 minutes and overnight by TLC. Even after 5 minutes incubation with DNA, trace amounts of exonuclease activity were observed (5 nM $^{32}$P primer/template and 10 nM 9° N. (exo⁻) DNA polymerase; 10 µl aliquot quenched with 10 µl 0.5M EDTA).

Figure 8:
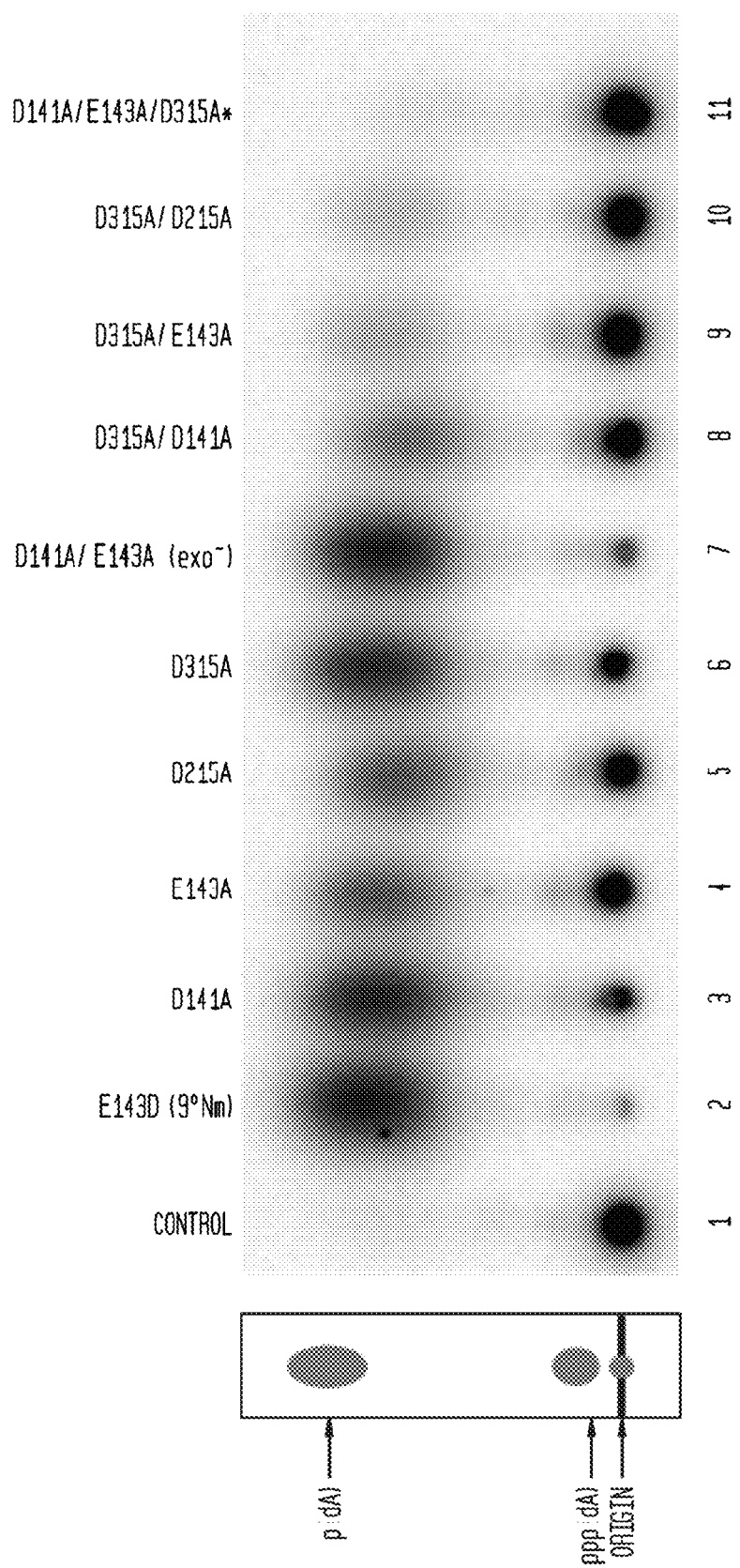

FIG. 8 shows that mutations in the 9° N DNA polymerase exonuclease active site modulate the levels of exonuclease activity. The assay described in FIGS. 5A and B was employed, using a final concentration of 0.2 units/pi (polymerase units) of the indicated DNA polymerase mutants.

Lane 1: control—no added polymerase;
Lane 2: 9° N (E143D);
Lane 3: 9° N (D141A);
Lane 4: 9° N (E143A);
Lane 5: 9° N (D215A);
Lane 6: 9° N (D315A);
Lane 7: 9° N (exo⁻) (D141A/E143A);
Lane 8: 9° N (D315A/D141A);
Lane 9: 9° N (D315A/E143A);
Lane 10: 9° N (D315A/D215A);
Lane 11: 9° N (D141A/E143A/D315A*).

Polymerases in lanes 8-11 are novel 9° N mutants described herein that have substantially diminished (Lanes 8-10) or no exonuclease activity (Lane 11 marked with an asterisk (*)).

Figure 9:
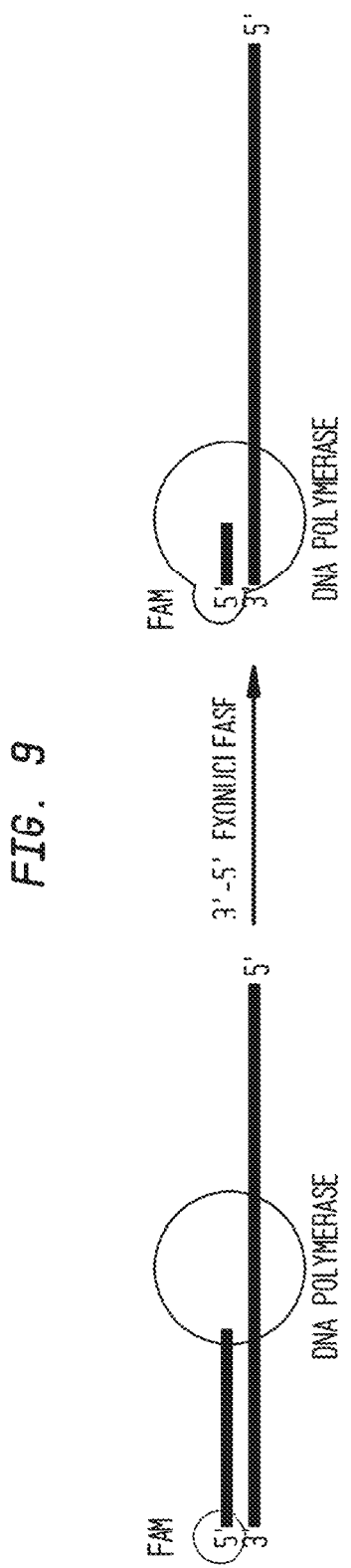

FIG. 9 shows a cartoon of a quantitative assay for 3'-5' exonuclease activity. Progressive shortening of a 5' fluorescently labeled double-stranded DNA substrate with a 5' overhang is measured by capillary electrophoresis.

Figure 10:
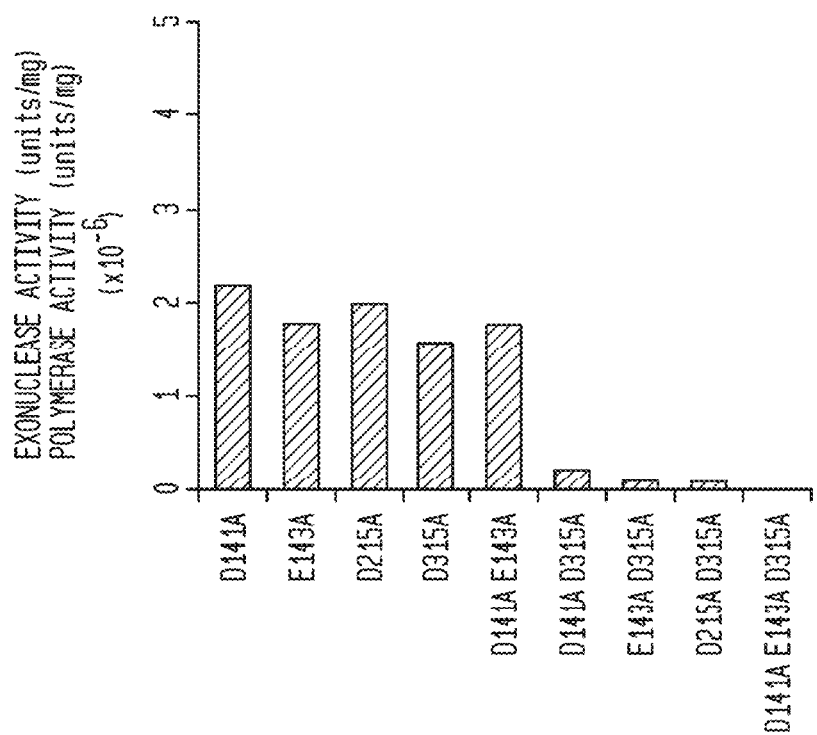

FIG. 10 shows the results of analyzing release of deoxynucleoside monophosphates (dNMPs) by 3'-5' exonuclease activity associated with a DNA polymerase using capillary electrophoresis. The ratio of exonuclease to 9° N polymerase activity (units/mg×10⁻⁶) is shown for 9 mutants identified on the X-axis to be D141A, E143A, D215A, D315A, D141A/E143A, D141A/D315A, E143A/D315A, D215A/D315A, and D141A/E143A/D315A.

FIG. 11A shows the amino acid sequence for 9° N (exo⁺) DNA polymerase (SEQ ID NO:1).

FIG. 11B shows the amino acid sequence for VENT (exo⁺) polymerase (SEQ ID NO:2).

FIG. 12A-12G shows that DNA polymerase exo-/- mutations reduce phasing and increase read quality in DNA sequencing-by-synthesis. Sequencing-by-synthesis of an *E. coli* MG1655 DNA library on the Illumina MiSeq instrument was completed using either purified wild type exo- (containing mutations in Exo I motif ((D141A/E143A); Table 1)) or mutant exo-/- (containing mutations in Exo I and Exo III motifs ((D141A/E143A/D315A); Table 1)) as the DNA sequencing polymerase.

FIG. 12A shows that mutant exo-/- (black) reduces phasing by an average of 5% overall and maximally by 15% after 150 cycles compared to wild type exo- (grey).

FIG. 12B shows a difference plot of the phasing compared between mutant exo-/- and wild type exo-.

FIG. 12C shows that average read quality was 12% higher with mutant exo-/- (black) compared to wild type exo- (grey).

FIG. 12D shows a difference plot of the quality score compared between mutant exo-/- and wild type exo-.

FIG. 12E shows the quality trimmed read length distribution for wild type exo-(grey) and mutant exo-/- (black). Reads were binned by length after quality trimming. Mutant exo-/- produced 10% longer trimmed reads compared to wild type exo-.

FIG. 12F shows that mutant exo-/- (black) produces 10% longer trimmed sequencing read lengths compared to wild type exo-(grey).

FIG. 12G shows that mutant exo-/- (black) produced 62% higher fraction of full length reads after quality trimming, compared to wild type exo- (grey).

DETAILED DESCRIPTION OF THE EMBODIMENTS

Family B DNA polymerases are a highly conserved family of enzymes. Archaeal DNA polymerases are Family B polymerases that characteristically have separate domains for DNA polymerase activity and 3'-5' exonuclease activity. The exonuclease domain is characterized by as many as six and at least three conserved amino acid sequence motifs in and around a structural binding pocket. Examples of archaeal polymerases include polymerases obtained from species of *Thermococcus, Pyrococcus* and *Sulfolobus*. During polymerization, nucleotides are added to the 3' end of the primer strand and during the 3'-5' exonuclease reaction, the primer is shifted to the 3'-5' exonuclease domain and the terminal bases are hydrolyzed.

Exonuclease-deficient (exo⁻) variants of these enzymes have been created over the past 20 years. However, our analysis of these alleged archaeal (exo⁻) DNA polymerase mutants revealed for the first time that these mutants surprisingly retain significant amounts of exonuclease activity. Using the assays described herein, variants that have no detectable exonuclease activity compared with the published exo⁻ DNA polymerases have been identified and are referred to herein as exo⁻/exo⁻ variants.

Figure 1:
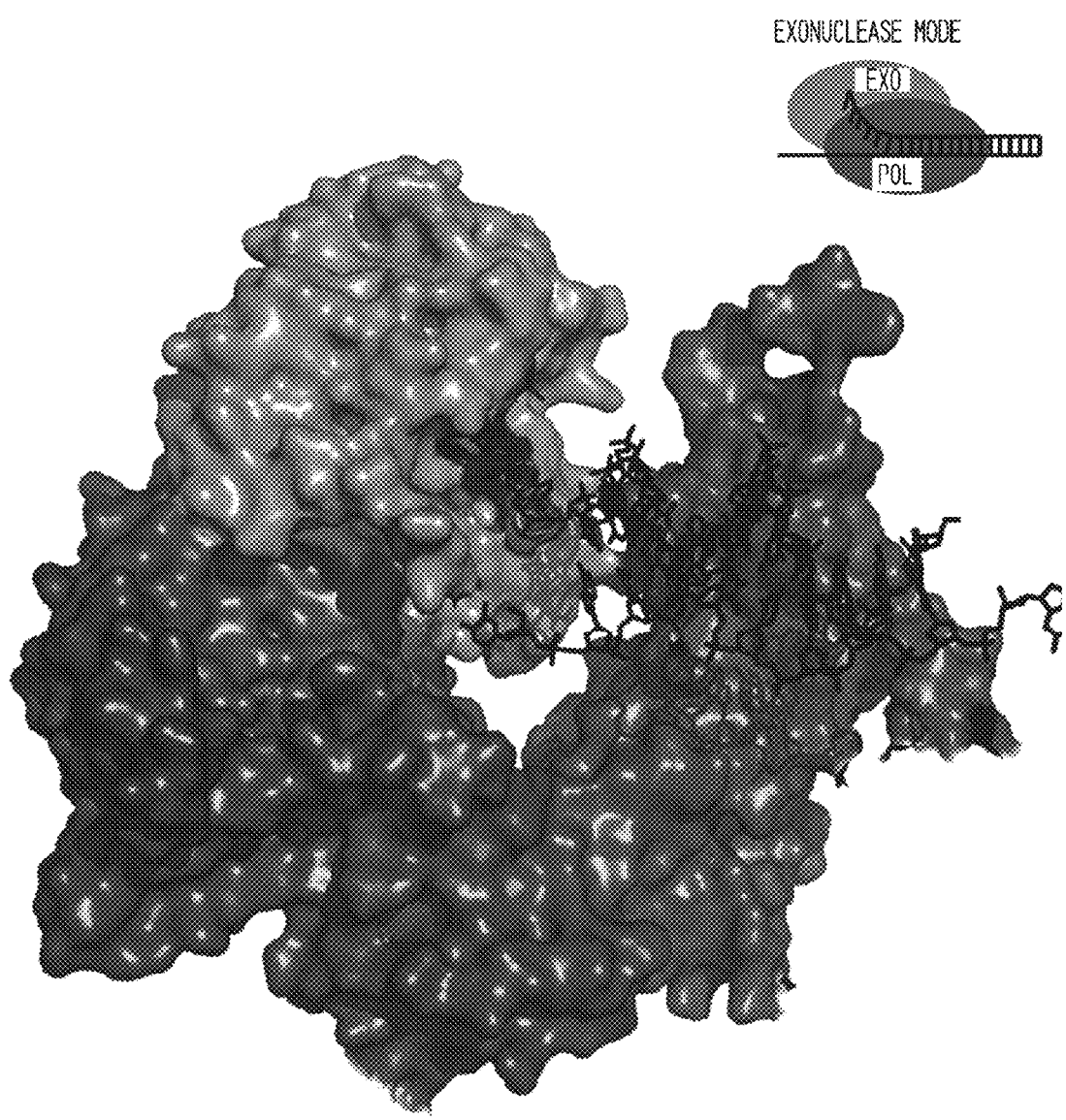
FIG. 1 shows the structure of RB69 DNA polymerase. The DNA substrate is shown with the 5' end positioned in the polymerase domain, and the 3' end extended toward the exonuclease domain (see inset cartoon).
Figure 2:
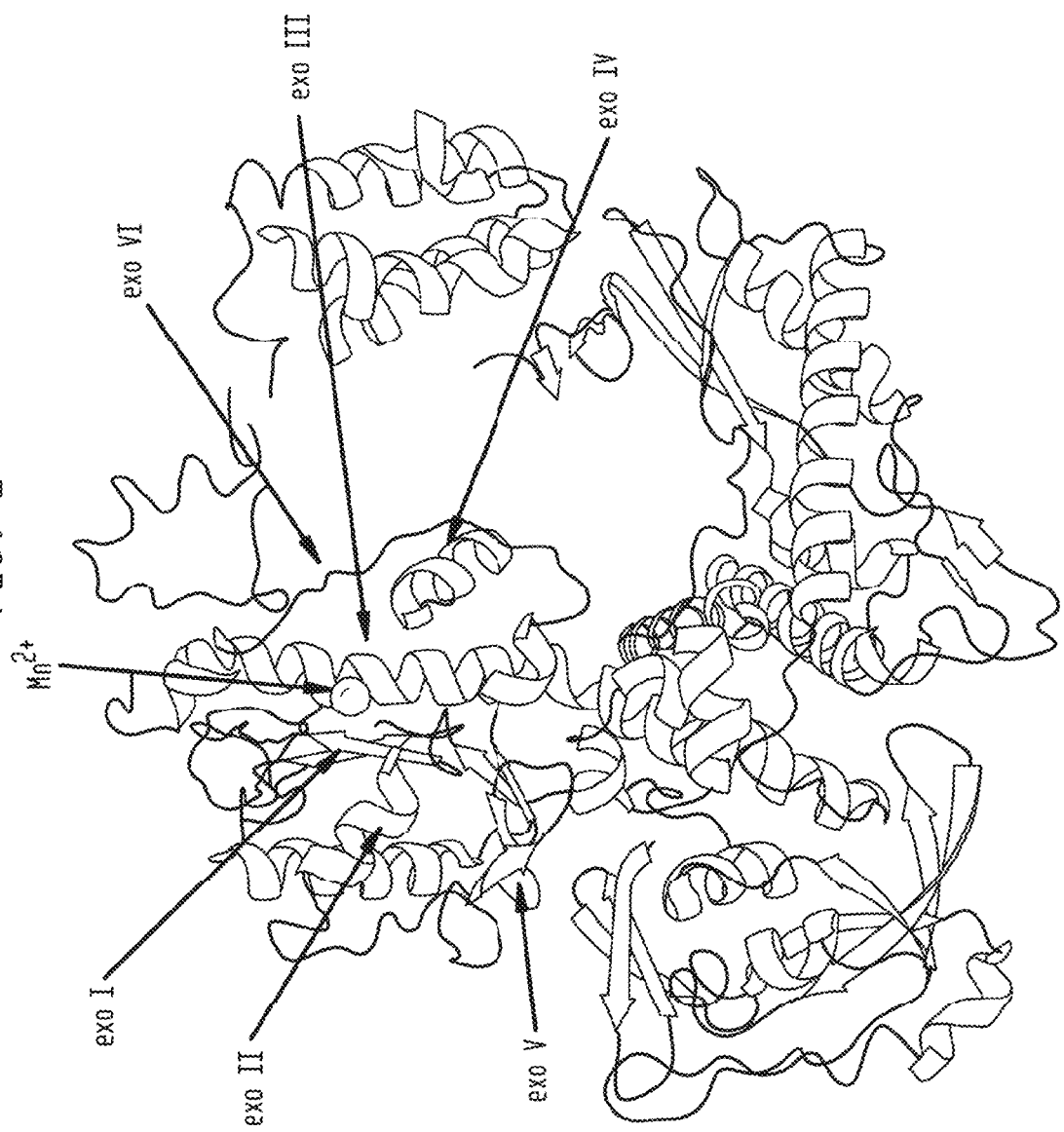
FIG. 2 shows a ribbon diagram of the exonuclease domain showing the location of the six exonuclease motifs (Exo I-VI) clustered around a centrally bound manganese ion. The structure is that of Pfu DNA polymerase (Research Collaboratory for Structural Bioinformatics Protein Data Bank (RCSB PDB) ID: 2JGU) (see website rcsb.org/pdb/home/home.do).
Figure 3:
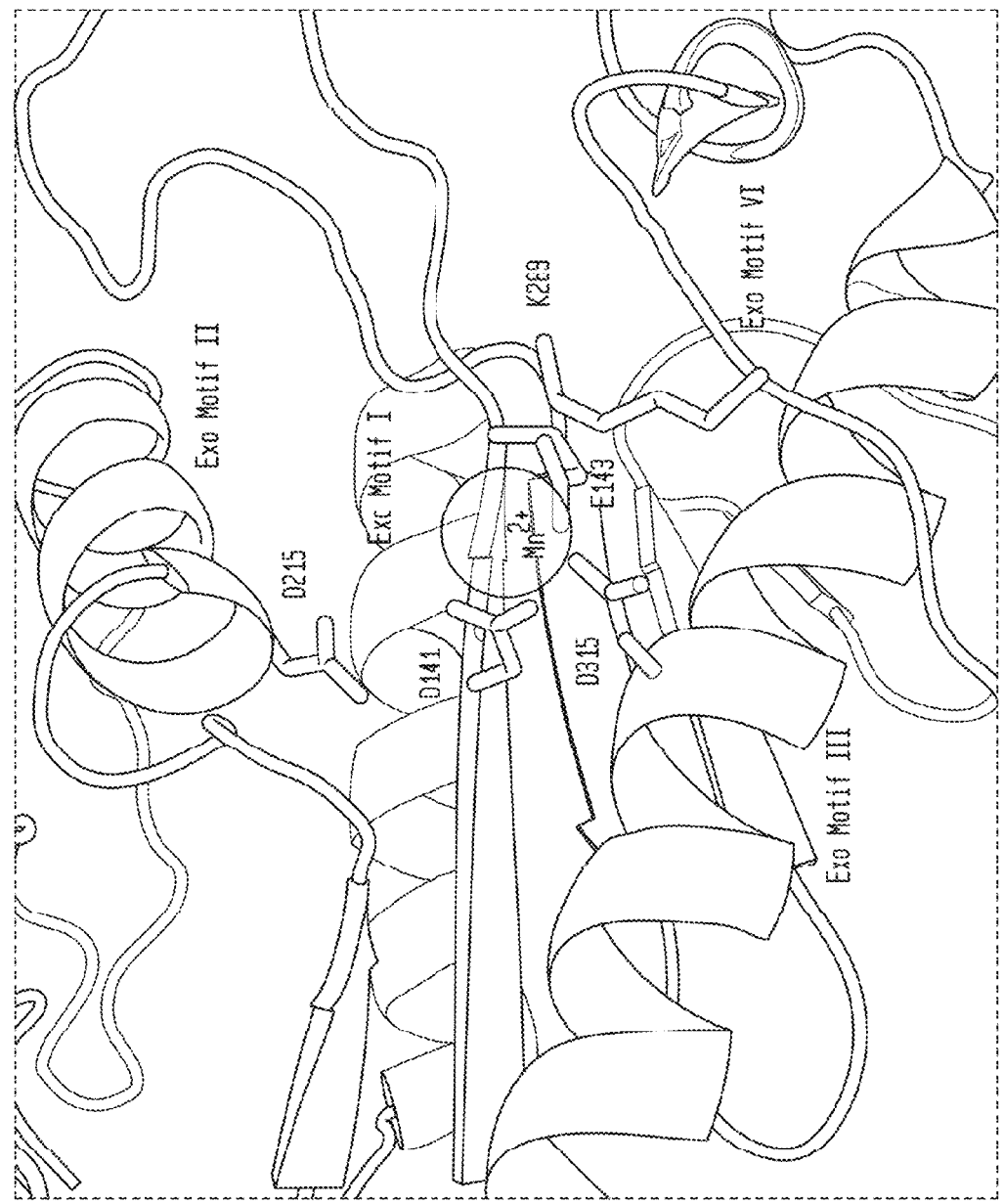
FIG. 3 shows a close-up view of FIG. 2, focused on the structure surrounding the bound manganese ion. The positions of D141, E143, D215, K289, D313, and D315 in Exo Motifs I, II, III and VI are shown.
Figure 4:
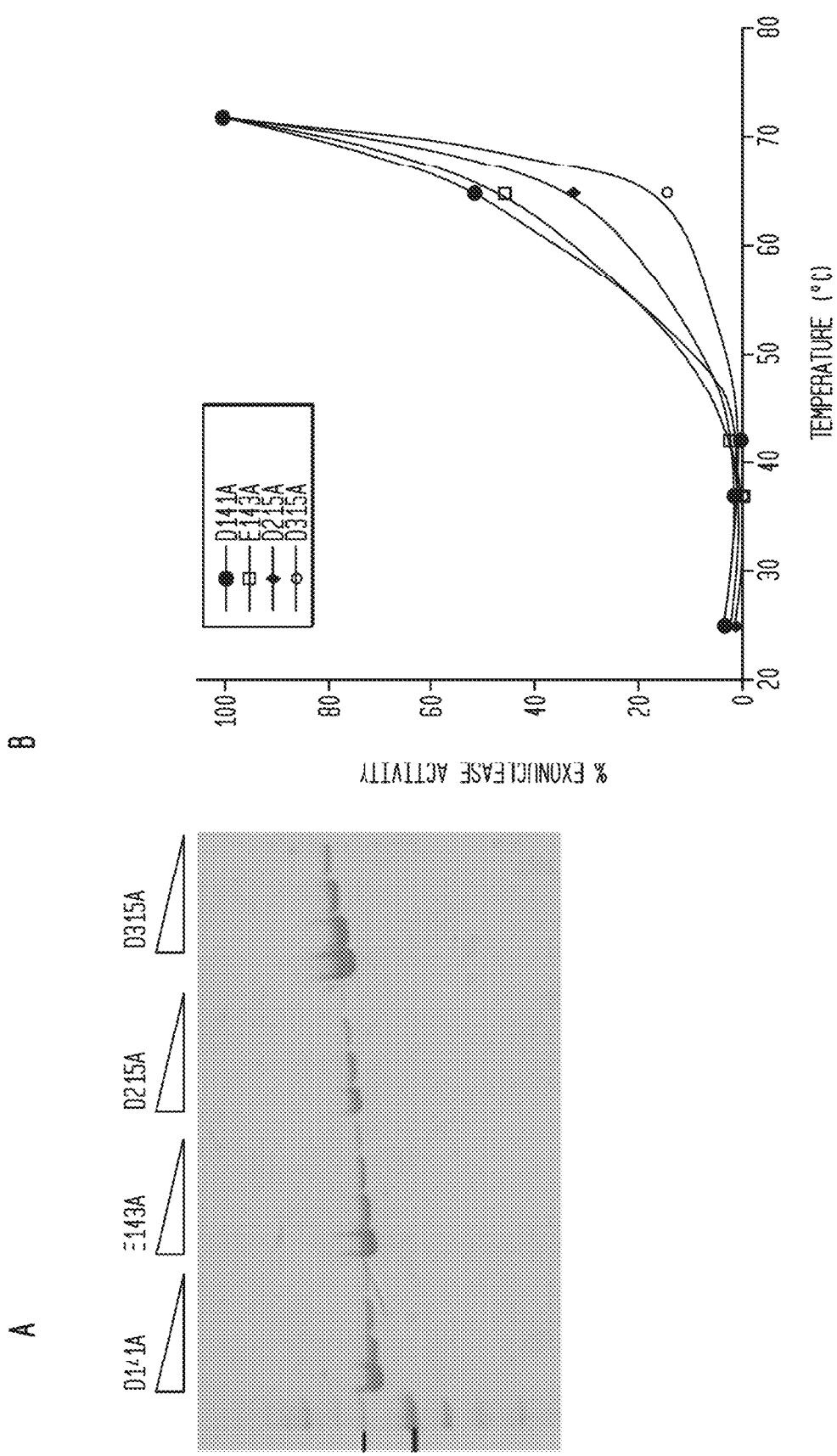
FIGS. 4A and B show purified DNA polymerase preparations with no detectable contaminating exonuclease activity.
FIG. 4B: Temperature profiles of the exonuclease activity of the four variants analyzed in FIG. 4A were determined using the assay described in Example 1. The results show that the exonuclease activity temperature profile mimics the thermophilic polymerization profile, further confirming that the contaminating exonuclease activity is related to the DNA polymerase and not the mesophilic *E. coli* host cell.

Parent archaeal polymerases are DNA polymerases that are isolated from naturally occurring organisms. The parent DNA polymerases share the property of having a structural binding pocket that binds and hydrolyses a substrate nucleic acid, producing 3'-dNMP. The structural binding pocket in this family of polymerases also shares the property of having sequence motifs which form the binding pocket, referred to as Exo Motifs I-VI. The location of Motifs I-VI in a three dimensional picture of the DNA polymerase is shown in FIGS. 1-3 and the highly conserved sequences in the motifs are shown in Table 1 below.

Additionally, parent DNA polymerases may contain three or more, four or more, or five or six of the following conserved amino acid sequences: LAFDIET (SEQ ID NO:3), ITYNGDNFD (SEQ ID NO:4), YSMEDA (SEQ ID NO:5), NLPTYTLEXVY (SEQ ID NO:6), IQRMGD (SEQ ID NO:7), and PKEKVYA (SEQ ID NO:8) or may have a sequence that is at least 80% or 85% or 90% or 95% identical to at least three, or four or five sequences selected from SEQ ID NOS:3-8.

"Synthetic" DNA polymerases refer to non-naturally occurring DNA polymerases such as those constructed by synthetic methods, mutated parent DNA polymerases such as truncated DNA polymerases and fusion DNA polymerases (e.g. U.S. Pat. No. 7,541,170). Variants of the parent DNA polymerase have been engineered by mutating single residues in any of Motifs I-VI using site-directed or random mutagenesis methods known in the art. The variant is then screened using the assays described herein to determine exonuclease activity. Those variants having an exonuclease activity/polymerase activity ratio of $0.2 \times 10^{-6}$ units/mg or less and optionally an exonuclease activity of 0.001 units/mg or less were deemed exo⁻/exo⁻ variants. Table 2 provides examples of exo⁻/exo⁻ variants that meet at least one of the above criterium. FIG. 8 shows how these mutants perform in the screening assay described in Example 1.

Single mutations or double mutations in Motif I described in the art for exo⁻ DNA polymerases were found to be insufficient to eliminate exonuclease activity.

In an embodiment, to form an exo⁻/exo⁻ DNA polymerase variant, one or more mutations may be introduced in the exonuclease active site within 10 Å, more specifically 6 Å, from the metal ion. If a mutation is introduced into the highly conserved sequences within Motif III (SEQ ID NO:5), then a second mutation may preferably occur in at least one of the highly conserved sequences in Motifs I-VI (in particular, SEQ ID NOS:3-8); or if a mutation is introduced into the highly conserved sequence in Motif I (SEQ ID NO:3), then a second mutation may be introduced into at least one of the highly conserved sequences in Motifs II-VI (in particular, SEQ ID NOS:4-8); or if a mutation is introduced into the highly conserved region in Motif III (in particular, SEQ ID NO:5), then a plurality of mutations may additionally be introduced into the highly conserved sequence in Motif I (SEQ ID NO:3) or in any of SEQ ID NOS:4 and 6-8; or if a mutation is introduced into the highly conserved region in Motif I (SEQ ID NO:3), then a plurality of mutations may additionally be introduced into any of the highly conserved sequences in motifs I-VI (SEQ ID NOS:3-8); to form an exo⁻/exo⁻ DNA polymerase variant.

Examples of mutations giving rise to an exo⁻/exo⁻ variant include mutations at positions in a parent polymerase corresponding to positions in SEQ ID NO:1 identified as follows: single mutations, K298 or K289, two or more mutations selected from D141, D215, and D315 or E143, D215, and D315 or three or more mutations selected from D141, E143, D215 and D315 wherein each mutant may additionally include a mutation of lysine at a position corresponding to K289 of SEQ ID NO:1. Mutations at the above sites may result in a replacement amino acid which is not the parent amino acid, for example, Alanine (A).

Mutations targeted to the conserved sequences described above, in the Examples and in Table 2 may include substitution of the amino acid in the parent amino acid sequences with a amino acid which is not the parent amino acid. For example, non-polar amino acids may be converted into polar amino acids (threonine, asparagine, glutamine, cysteine, tyrosine, aspartic acid, glutamic acid or histidine) or the parent amino acid may be changed to an alanine.

Alternatively, mutations may be randomly generated within the various motifs (within or outside the highly conserved sequences described in SEQ ID NOS:3-8) using standard techniques known in the art and the resultant enzymes can be tested using the sensitive assays described in the Examples to determine whether they have substantially no exonuclease activity.

Exo Motifs I-VI are defined below where "x" is any amino acid, "n" is a non-polar amino acid (e.g., glycine, alanine, valine, leucine, isoleucine, proline, methionine, phenylalanine, tryptophan) and "p" is a polar amino acid (e.g., serine, threonine, asparagine, glutamine, cysteine, tyrosine, aspartic acid, glutamic acid, lysine, arginine, histidine).

Exo Motif I contains the conserved amino acid sequence xxnDxExxx. In one embodiment, the conserved sequence corresponds to amino acids 138-144 (LAFDIET (SEQ ID NO:3)) in SEQ ID NO:1. In one embodiment, a mutation is targeted to at least one of an amino acid corresponding to D141 and E143 in SEQ ID NO:1.

Exo Motif II contains the conserved amino acid sequence nxYNxpxFDnnY (SEQ ID NO:11). In one embodiment, the conserved sequence corresponds to amino acids 207-215 (ITYNGDNFD (SEQ ID NO:4)) in SEQ ID NO:1. In one embodiment, a mutation is targeted to an amino acid corresponding to D215 in SEQ ID NO:1.

Exo Motif III contains the conserved amino acid sequence nnpYxxxDnxx. In one embodiment, the conserved sequence corresponds to amino acids 311-316 (YSMEDA (SEQ ID NO:5)) in SEQ ID NO:1. In one embodiment, a mutation is targeted to an amino acid corresponding to D315 in SEQ ID NO:1.

Exo Motif IV contains the conserved motif xxpYpLpxVx. In one embodiment, the conserved sequence corresponds to amino acids 269-279 (NLPTYTLEXVY (SEQ ID NO:6)) in SEQ ID NO:1. In one embodiment, a mutation is targeted to at least one of an amino acid corresponding to T274 and T276 in SEQ ID NO:1.

Exo Motif V contains the conserved motif: IxxxGpxx. In one embodiment, the conserved sequence corresponds to amino acids 241-246 (IQRMGD (SEQ ID NO:7)) in SEQ ID NO:1.

Exo Motif VI contains the conserved exonuclease/polymerase motif xKpKnnn. In one embodiment, the Exo Motif VI corresponds to amino acids 286-292 (PKEKVYA (SEQ ID NO:8)) in SEQ ID NO:1.

TABLE 1

Conserved sequences in the exonuclease motifs for representative archaeal polymerases

| Species | Accession number | | | | | | |
|---------|------------------|---|---|---|---|---|---|
| Thermococcus species 9° N | Q56366 | LAFDIET (SEQ ID NO: 3) | ITYNGDNF D (SEQ ID NO: 4) | YSMEDA (SEQ ID NO: 5) | NLPTYT LEXVY (SEQ ID NO: 6) | IQRMG D (SEQ ID NO: 7) | PKEKVYA (SEQ ID NO: 8) |
| Thermococcus gammatolerans EJ3 | YP_002959821 | LAFDIET | ITYNGDNF D | YSMEDA | NLPTYT LEXVY | IQRMG D | PKEKVYA |

TABLE 1-continued

Conserved sequences in the exonuclease motifs for representative archaeal polymerases

| | | I | II | III | IV | V | VI |
|---|---|---|---|---|---|---|---|
| Thermococcus guaymasensis | ACQ99189 | LAFDIET | ITYNGDNFD | YSMEDA | NLPTYT LEXVY | IQRMGD | PKEKVYA |
| Thermococcus gorgonarius | P56689 | LAFDIET | ITYNGDNFD | YSMEDA | NLPTYT LEXVY | IQRMGD | PKEKVYA |
| Thermococcus kodakaraensis | 1WNS_A | LAFDIET | ITYNGDNFD | YSMEDA | NLPTYT LEXVY | IQRMGD | PKEKVYA |
| Desulfurococcus sp. Tok | Q7SIG7 | LAFDIET | ITYNGDNFD | YSMEDA | NLPTYT LEXVY | IQRMGD | PKEKVYA |
| Thermococcus sp. AM4 | YP_002582532 | LAFDIET | ITYNGDNFD | YSMEDA | NLPTYT LEXVY | IQRMGD | PKEKVYA |
| Thermococcus marinus | ACR33068 | LAFDIET | ITYNGDNFD | YSMEDA | NLPTYT LEXVY | IQRMGD | PKEKVYA |
| Thermococcus thioreducens | ABK59374 | LAFDIET | ITYNGDNFD | YSMEDA | NLPTYT LEXVY | IQRMGD | PKEKVYA |
| Thermococcus hydrotherma-lis | Q9HH84 | LAFDIET | ITYNGDNFD | YSMEDA | NLPTYT LEXVY | IQRMGD | PKEKVYA |
| Thermococcus waiotapuensis | AFC60629 | LAFDIET | ITYNGDNFD | YSMEDA | NLPTYT LEXVY | IQRMGD | PKEKVYA |
| Thermococcus zilligii | ABD14868 | LAFDIET | ITYNGDNFD | YSMEDA | NLPTYT LEXVY | IQRMGD | PKEKVYA |
| Thermococcus fumicolans | P74918 | LAFDIET | ITYNGDNFD | YSMEDA | NLPTYT LEXVY | IQRMGD | PKEKVYA |
| Thermococcus literalis | ADK47977 | LAFDIET | ITYNGDNFD | YSMEDA | NLPTYT LEXVY | IQRMGD | TKSKLG (SEQ 12) |
| Motifs I-VI | | I | II | III | IV | V | VI |
| | | xxnDxExxx | nxYnxpxFDnnY (SEQ ID NO: 11) | nnpYxxxDnxx | xxpYpLpxVx | IxxxGpxx | xKpKnnn |

All references cited herein, as well as U.S. Provisional Application No. 61/484,731 filed May 11, 2011, are hereby incorporated by reference.

EXAMPLES

Example 1

Sensitive Assays to Detect Exonuclease and Pyrophosphorlysis Activities in Exo⁻ DNA Polymerase Mutants (a) Monitoring the 3' Degradation of a Primer by a DNA Polymerase to Distinguish Exonuclease Action (Release of dAMP) from Pyrophosphorylsis (Release of dATP)

3'-[alpha-$^{32}$P]-dAMP-labeled primer:template DNA substrate ($^{32}$P-dA P/T) was prepared by incorporating [alpha-$^{32}$P]-dATP (75 nM) into a primer CGCCAGGGTTTTC-CCAGTCACGAC (SEQ ID NO:9) and template AACCGGTTACGTACGTACGTGTCGT-GACTGGGAAAACCCTGGCG (SEQ ID NO:10) (75 nM) using Klenow (exo⁻) DNA polymerase (0.2 units/μl) (NEB, Ipswich, Mass.) in 1×NEBuffer 2 (50 mM NaCl, 10 mM Tris-HCl (pH 7.9 @ 25° C.), 10 mM MgCl$_2$, 1 mM dithiothreitol) (NEB, Ipswich, Mass.) for 30 minutes at 37° C. Following the reaction, Klenow (exo⁻) DNA polymerase was heat-inactivated at 65° C. for 20 minutes. Unincorporated [alpha-$^{32}$P]-dATP was separated by gel filtration (Princeton Separations, Freehold, N.J.).

To measure the release of the terminal 3' [alpha-$^{32}$P]-dAMP, 10 μL of diluted polymerase was added to 10 μL of a solution containing 10 nM $^{32}$P-dA P/T in 2× ThermoPol™ buffer (NEB, Ipswich, Mass.). Reaction products were separated by PEI-cellulose thin layer chromatography using 0.5 M LiCl$_2$ as the solvent. Dried plates were exposed to a storage phosphor screen (GE Healthcare, Waukesha, Wis.) and imaged on a Typhoon® 9400 scanner (GE Healthcare Biosciences, Uppsala, Sweden). The product of the DNA polymerase 3'-5' exonuclease reaction is [alpha-$^{32}$P]-dAMP, which migrates faster than [alpha-$^{32}$P]-dATP or $^{32}$P-dA P/T when analyzed by PEI-cellulose TLC. As a control for exonuclease activity, VENT (exo⁺) DNA polymerase (0.2 units/μL) was incubated with $^{32}$P-dA P/T (10 nM) in 1× ThermoPol buffer in the absence of dNTPs and is expected to remove the [alpha-$^{32}$P]-dAMP by the inherent 3'-5' exonuclease activity.

(b) Monitoring Degradation of a 5' 6-Carboxyfluorescein (FAM)-Labeled DNA Primer Annealed to an Unlabeled DNA Template In this assay, the 3'-5' exonuclease activity of 9° N DNA polymerase variants was tested by monitoring degradation of a FAM-labeled DNA primer annealed to an unlabeled DNA template (FIG. 9). Reactions were prepared by adding 10 μL of diluted DNA polymerase to 10 μL of a solution containing 0.1 μM FAM-labeled DNA substrate, 18 mM $MgSO_4$ and 2× ThermoPol buffer (40 mM Tris-HCl, 20 mM $(NH_4)_2SO_4$, 20 mM KCl, 4 mM $MgSO_4$, 0.1% TRITON® X-100, pH 8.8 (Union Carbide Corporation, Midland, Mich.)). Samples were incubated at 72° C. for 200 min and quenched with an equal volume of 0.5 M EDTA. Conversion of the fluorescently labeled DNA primer-template to shorter 3'-5' exonuclease products was monitored by capillary electrophoresis using an AB3730xl DNA analyzer (Applied Biosystems, now Life Technologies, Carlsbad, Calif.). Fluorescence was quantified and analyzed using Peak Scanner™ Software v1.0 (Applied Biosystems, now Life Technologies, Carlsbad, Calif.). One unit of 3'-5' exonuclease activity was defined as the amount of enzyme required to release 10 nmol of dNMP in 30 minutes at 72° C.

(c) Measurement of DNA Polymerase Activity

DNA polymerase activity was assayed by measuring the incorporation of [$^{32}$P]-dCMP into a primed single-stranded M13 DNA substrate as described previously (Gardner and Jack, *Nucleic Acids Research* 27(12): 2545-2553 (1999)). Reactions were prepared by adding 1.5 μL of diluted enzyme to 28.5 μL, resulting in a solution containing 15 nM primed M13mp18 DNA, 1× ThermoPol buffer, 0.2 mM dNTP, and 20 μCi [$^{32}$P]-dCTP. The reactions were incubated at 75° C. for 30 min, spotted onto 3 mm Whatman® filter discs (Whatman Paper, Kent, England), precipitated and washed with cold 10% TCA, rinsed with 95% ethanol and then dried. Incorporated [$^{32}$P]-dCTP was quantified using a scintillation counter. Polymerase activity was calculated as the amount of [$^{32}$P]-dCMP incorporated. One unit of DNA polymerase activity was defined as the amount of enzyme that will incorporate 10 nmol of dNMP in a total reaction volume of 50 μL in 30 minutes at 75° C. in 1× ThermoPol Reaction Buffer.

Example 2

Assays to Monitor Polymerase to Exonuclease Partitioning

Three-dimensional structures of DNA polymerases in complex with a DNA oligonucleotide primer and template show that the primer strand is either annealed to the template strand in the polymerase domain or unpaired from the template strand in the 3'-5' exonuclease pocket. An assay was designed to measure the distribution of polymerase/DNA complexes in the exonuclease as opposed to polymerization configurations. With this assay, polymerase variants can be assayed to assess how well they block binding of the primer strand in the 3'-5' exonuclease pocket, thereby eliminating 3'-5' exonuclease activity.

A primer oligonucleotide was modified on the 3' terminus with a 2-aminopurine nucleoside that is naturally fluorescent. 2-aminopurine fluorescence on such a primer was quenched when annealed to a template strand in the polymerase active site. However, when situated in the 3'-5' exonuclease pocket, the primer adopted a single-stranded configuration, was not quenched, and thus produced high levels of 2-aminopurine fluorescence. Therefore, using these characteristics, the position of the 2-aminopurine oligonucleotide in either the polymerase or 3'-5' exonuclease site can be monitored by fluorescence spectroscopy.

DNA polymerase variants that block oligonucleotide partitioning to the 3'-5' exonuclease pocket have low 2-aminopurine fluorescence because the 2-aminopurine oligonucleotide remains annealed to the template strand in the polymerase active site and therefore quenched.

DNA variants were constructed by mutating amino acids comprising Exo Motif IV and Exo Motif V and/or Exo Motif VI.

DNA polymerase variants that block oligonucleotide partitioning to the 3'-5' exonuclease pocket were tested for 3'-5' exonuclease activity using the TLC assay described. If the oligonucleotide was sterically blocked from the 3'-5' exonuclease pocket, then 3'-5' exonuclease activity was abolished.

Example 3

Identification of Exo⁻/Exo⁻ DNA Polymerase Variants

To test if a third conserved aspartate (D315) in Exo Motif III contributed to the observed exonuclease activity in DNA polymerases with mutations in Exo Motif I, site-directed mutagenesis was used to change D315 to alanine in DEEP VENT (GenBank: 825735) and 9° N DNA polymerases (SEQ ID NO:1). Deep Vent D141A/E143A/D315A and 9° N D141A/E143A/D315A triple mutants were constructed, expressed, and purified as described by Gardner and Jack (*Nucleic Acids Research* 27(12): 2545-2553 (1999)) with minor modifications including the addition of a size-exclusion column as a final purification step to remove any contaminating exonucleases.

The third exonuclease-active site aspartic acid in Exo Motif III when mutated to alanine (D315A), in combination with Exo Motif I mutants D141A/E143A, was shown to remove 3'-5' exonuclease activity or to significantly reduce 3'-5' exonuclease activity to below detectable levels as determined by this assay (See FIG. 7). Such exo⁻ DNA polymerases could reduce primer degradation in methods such as sequencing by synthesis.

Example 4

Method to Determine Essential Amino Acids for Mutation to Remove Exonuclease Activity In this method, a divalent metal ion bound in the 3'-5' exonuclease binding pocket and MacPymol software (Schrödinger, New York, N.Y.) were used to identify amino acids within 6 Å of the divalent metal ions that were also found in Exo Motifs I, II, and III. For example, using the Pfu DNA polymerase three-dimensional structure (RCSB PDB ID: 2JGU), amino acids within 6 Å of the bound $Mn^{2+}$ ion were identified as follows: Exo Motif I (D141, 1142, E143), Exo Motif II (F214, D215), Exo Motif III (Y311, D315) and Exo Motif VI (K289).

By making mutants and assaying the activity of the mutants, the exonuclease activity and exonuclease activity/polymerase activity ratio could be determined. (One unit of exonuclease activity was defined as the amount of enzyme required to release 10 nmol of dNMP in 30 minutes at 72° C. One unit of DNA polymerase activity was defined as the amount of enzyme that will incorporate 10 nmol of dNMP in a total reaction volume of 50 μL in 30 minutes at 75° C. in 1× ThermoPol Reaction Buffer).

Example 5

Engineered DNA Polymerase Variants Abolish Exonuclease Activity for Sequencing by Synthesis In DNA sequencing by synthesis, a DNA polymerase extends a DNA substrate with a fluorescently labeled reversible nucleotide terminator. Synchronous synthesis among all the identical templates was maintained to ensure a homogenous fluorescent signal. Residual degradation of DNA by a DNA polymerase 3'-5' exonuclease activity may cause certain templates to lag behind others. Progressive accumulation of DNA molecules, which are either shorter or longer than the majority of the molecules, is called phasing. Phasing can be caused by incomplete chemical reversal of blocking groups, incomplete primer extension, incorporation of an unlabeled or unblocked dNTP, or residual pyrophosphorolysis or 3'-5' exonuclease activity. Phasing leads to a heterogenous signal, thereby limiting sequencing read length. The phasing rate was reported at 0.5% per cycle (Kircher et al. Genome Biology 10(8), R83 (2009), doi:10.1186/gb-2009-10-8-r83) in the Illumina sequencing by synthesis system.

next sequencing cycle to proceed. Sequencing cycles continue to read lengths of up to hundreds of base pairs.

During DNA sequencing-by-synthesis, it is preferable that repeated incorporations be close to 100% efficiency so that extension is synchronous over all the molecules of the sample (Fuller, Middendorf et al. 2009). Progressive accumulation of DNA molecules that are either shorter (phasing) or longer (pre-phasing) than the majority of the molecules leads to a heterogeneous signal, sequence quality decay, lower confidence base calls, and shorter overall sequencing reads. In the Illumina sequencing-by-synthesis system, the phasing rate is reported at 0.5% per cycle and is a major contributor to limits on DNA sequencing read length (Kircher, Stenzel et al. 2009).

TABLE 2

DNA polymerases lacking residual 3'-5' exonuclease activity may reduce phasing and improve DNA sequencing read length

| DNA polymerase | Exonuclease activity (Units/mg)[1] | Polymerase activity (Units/mg)[2] | Exonulease activity (Units/mg) / Polymerase activity (Units/mg) |
|---|---|---|---|
| D141A | 0.050 | $2.3 \times 10^4$ | $2.2 \times 10^{-6}$ |
| E143A | 0.064 | $4.0 \times 10^4$ | $1.8 \times 10^{-6}$ |
| D215A | 0.035 | $1.8 \times 10^4$ | $1.9 \times 10^{-6}$ |
| D315A | 0.031 | $2.0 \times 10^4$ | $1.6 \times 10^{-6}$ |
| D141A E143A | 0.079 | $4.5 \times 10^4$ | $1.8 \times 10^{-6}$ |
| D141A D315A | 0.064 | $3.1 \times 10^4$ | $0.20 \times 10^{-6}$ |
| E143A D315A | 0.0014 | $1.9 \times 10^4$ | $0.074 \times 10^{-6}$ |
| D215A D315A | 0.0020 | $3.6 \times 10^4$ | $0.056 \times 10^{-6}$ |
| D141A E143A D315A | 0.00073 | $4.7 \times 10^4$ | $0.015 \times 10^{-6}$ |

[1]One unit of exonuclease activity was defined as the amount of enzyme required to release 10 nmol of dNMP in 30 minutes at 72° C.
[2]One unit of DNA polymerase activity was defined as the amount of enzyme that will incorporate 10 nmol of dNMP in a total reaction volume of 50 μL in 30 minutes at 75° C. in 1 × ThermoPol Reaction Buffer.

DNA polymerases developed for next generation sequencing by synthesis have a double mutation in the Exo Motif I (D141A/E143A) (WO 2007/052006 A1, WO 2008/023179 A2) and retain residual 3'-5' exonuclease activity. These DNA polymerases are replaced with exo−/exo− DNA polymerase variants to improve the reliability of next generation sequencing by synthesis. The exo−/exo− DNA polymerase variants may also be used for improved SNP detection which relies on stable incorporation of modified nucleotides.

Example 6

Exo−/− DNA Polymerases Reduce Phasing and Increase Read Quality and Length During DNA Sequencing-by-Synthesis In cyclic reversible termination (CRT) DNA sequencing-by-synthesis methods such as the Illumina MiSeq and HiSeq instruments, a DNA polymerase extends many DNA strands in parallel with modified nucleotide terminators having unique fluorescent groups for each base and a reversible terminating group at the 3'-hydroxyl position. Because of this terminating group, the DNA polymerase only incorporates a single base at each cycle. Following incorporation, the base is identified by fluorescent detection. Chemical cleavage of the terminating moiety leaves a 3'-hydroxyl group, allowing the Even a small amount of residual 3'-5' exonuclease activity in the DNA polymerase used during extension could excise an added base before imaging and contribute to phasing and read-length limitations. Therefore, if residual 3'-5' exonuclease activity is abolished in the sequencing DNA polymerase (as taught in Examples 2-5) then sequencing-by-synthesis phasing rates decrease resulting in higher quality and longer sequencing reads. As evidence of this general benefit, DNA sequencing of a 500 bp insert E. coli MG1655 DNA library was performed on the Illumina MiSeq using either purified wild type exo− (containing mutations in Exo I motif ((D141A/E143A); Table 1)) or mutant exo−/− (containing mutations in Exo I and Exo III motifs ((D141A/E143A/D315A); Table 1)).

The phasing rate, read quality, and read length distribution were calculated (FIG. 12). Phasing information was extracted from the EmpiricalPhasingCorrection files produced by Illumina RTA (version 1.17.28). Data from all tiles was averaged. Average quality was calculated for each read position using the fastx_quality_stats tool (v0.0.10) (Gordon, 2014). Fastq reads generated by the Illumina Casava Pipeline (1.9) were trimmed using Sickle (v1.200) (Joshi, 2014) requiring a Q30 average quality over a 20 bp window. The percentage of reads passing filters (pf) was calculated for windows greater than 20 bp. Length 0 corresponds to the percentage of pf reads that were discarded. Trimmed and untrimmed reads were aligned against the *E. coli* K12 MG1655 reference sequence using Bowtie v 2.10 (Joshi, 2014; Langmead & Salzberg, 2012) using the "end to end" and "sensitive" options. All data was plotted using Tableau Desktop (version 8.1.0).

Compared to a sequencing run with wild type exo−, mutant exo−/− decreased phasing rate by for example, an average of 5%-15% after cycle 150 (FIGS. 12 A and B). As a result of lower phasing rates, mutant exo−/− were shown in one example to produce sequencing reads with an average of 12% higher quality scores compared to wild type exo− (FIGS. 12 C and D). Lower phasing rates and higher quality reads produced with mutant exo−/− resulted in one example, an average of 10% longer sequencing read lengths (FIGS. 12 E, F, and Table 3) and a higher fraction of full length reads (FIG. 12 G).

TABLE 3

A summary of alignment statistics for MiSeq DNA sequencing by synthesis with either wild type exo − or mutant exo −/−.

| Run | Average Read Length | # Reads | # Aligned Reads | % Aligned Reads |
| --- | --- | --- | --- | --- |
| Mutant exo −/− | 192 | 7,277,135 | 6,788,620 | 93.30% |
| Wild-type exo − | 177 | 6,848,822 | 6,338,947 | 92.60% |

What is claimed is:

1. A variant of a parent polymerase wherein
   (i) the parent polymerase has at least 90% sequence homology with SEQ ID NO:1 and/or SEQ ID NO:2,
   (ii) a difference between the parent polymerase and the variant comprises an amino acid mutation in SEQ ID NO:5 at position 5 and at least one amino acid mutation in at least one amino acid sequence selected from SEQ ID NOS: 3, 4, 6 and 8; and
   (iii) wherein the variant is characterized by one or more properties selected from: reducing average phasing by 1%-51% compared to the parent polymerase; increasing average sequencing read quality by 7%-75% compared to parent enzyme; increasing average sequencing read length by 1%-200% and increasing average full length sequencing reads by 25%-200%.

2. A variant according to claim 1 wherein the variant is characterized by one or more properties selected from: reducing average phasing by at least 1%-10% compared to the parent polymerase; increasing average sequencing read quality by at least 10%-50% compared to parent enzyme; increasing average sequencing read length by at least 5%-20% and increasing average full length sequencing reads by at least 25%-100%.

3. A method of amplifying DNA in the absence of exonuclease activity, comprising: combining a variant of a parent polymerase wherein the parent polymerase has at least 90% sequence homology with SEQ ID NO:1 and/or SEQ ID NO:2, and wherein a difference between the parent polymerase and the variant comprises an amino acid mutation in SEQ ID NO:5 at position 5 and at least one amino acid mutation in at least one amino acid sequence selected from SEQ ID NOS: 3, 4, 6 and 8, with a template DNA and a primer; and amplifying the DNA.

4. A method of sequencing a polynucleotide, comprising:
   (a) combining a variant of a parent polymerase wherein the parent polymerase has at least 90% sequence homology with SEQ ID NO:1 and/or SEQ ID NO:2, and wherein a difference between the parent polymerase and the variant comprises an amino acid mutation in SEQ ID NO:5 at position 5 and at least one amino acid mutation in at least one amino acid sequence selected from SEQ ID NOS: 3, 4, 6 and 8 with a template polynucleotide and at least one primer to form a hybridized polynucleotide;
   (b) permitting the variant polymerase to incorporate into the template-primer hybrid, a modified nucleotide that is complementary to a nucleoside at the corresponding position on the template;
   (c) identifying the nucleoside at the corresponding position on the template; and
   (d) optionally repeating (a) through (c).

5. A method according to claim 4 wherein the variant is characterized by one or more properties selected from: reducing average phasing by 1%-51% compared to the parent polymerase; increasing average sequencing read quality by 7%-75% compared to parent enzyme; increasing average sequencing read length by 1%-200% and increasing average full length sequencing reads by 25%-200%.

6. A method according to claim 4, wherein the variant is characterized by one or more properties selected from: reducing average phasing by at least 1%-10% compared to the parent polymerase; increasing average sequencing read quality by at least 10%-50% compared to parent enzyme; increasing average sequencing read length by at least 5%-20% and increasing average full length sequencing reads by at least 25%-100%.

7. A method according to claim 4 wherein (d) further comprises at least one of: reducing average phasing by 1%-51% compared to the parent polymerase; increasing average sequencing read quality by 7%-75% compared to parent enzyme; increasing average sequencing read length by 1%-200% or increasing average full length sequencing reads by 25%-200%.

8. A method according to claim 4 wherein (d) further comprises at least one of: reducing average phasing by at least 1%-10% compared to the parent polymerase; increasing average sequencing read quality by at least 10%-50% compared to parent enzyme; increasing average sequencing read length by at least 5%-20% and increasing average full length sequencing reads by at least 25%-100%.

\* \* \* \* \*